(12) United States Patent
Kirsch et al.

(10) Patent No.: US 6,706,338 B2
(45) Date of Patent: Mar. 16, 2004

(54) LIQUID-CRYSTALLINE COMPOUNDS

(75) Inventors: Peer Kirsch, Darmstadt (DE); Florian Huber, München (DE); Joachim Krause, Dieburg (DE); Michael Heckmeier, Bensheim (DE); Detlef Pauluth, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/024,501

(22) Filed: Dec. 21, 2001

(65) Prior Publication Data

US 2003/0230737 A1 Dec. 18, 2003

(30) Foreign Application Priority Data

Dec. 23, 2000 (DE) .......................... 100 64 996

(51) Int. Cl.[7] .................. C09K 19/30; C09K 19/20; C07C 69/76; C07C 25/13
(52) U.S. Cl. ............... 428/1.1; 252/299.63; 252/299.67; 560/64; 560/65; 570/127; 570/129
(58) Field of Search ....................... 428/1.1; 252/299.63, 252/299.67; 560/64, 65; 570/127, 129

(56) References Cited

U.S. PATENT DOCUMENTS 6,287,648 B1 * 9/2001 Tarumi et al. ................ 428/1.1
6,468,608 B1 * 10/2002 Bremer et al. ............... 428/1.1

FOREIGN PATENT DOCUMENTS

| DE | 4015681 | * 11/1991 |
| JP | 5-331084 | * 12/1993 |
| WO | WO 99/50210 | * 10/1999 |

* cited by examiner

Primary Examiner—Shean C. Wu
(74) Attorney, Agent, or Firm—Millen, White, Zelano & Branigan, P.C.

(57) ABSTRACT

The invention relates to liquid-crystalline compounds of the formula I,

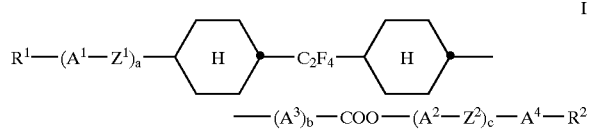

and to liquid-crystalline media comprising at least one compound of the formula I and to electro-optical displays containing such a liquid-crystalline medium.

17 Claims, No Drawings

LIQUID-CRYSTALLINE COMPOUNDS

The present invention relates to liquid-crystalline compounds and to a liquid-crystalline medium, to its use for electro-optical purposes and to displays containing said medium.

Liquid crystals are used especially as dielectrics in display devices, as the optical properties of such substances can be affected by an applied voltage. Electro-optical devices on the basis of liquid crystals are very well known to those skilled in the art and can be based on various effects. Examples of such devices include cells with dynamic scattering, DAP cells (deformation of aligned phases), guest/host cells, TN cells having a twisted nematic structure, STN cells (supertwisted nematic), SBE cells (superbirefringence effect) and OMI cells (optical mode interference). The most common display devices are based on the Schadt-Helfrich effect and have a twisted nematic structure.

The liquid crystal materials must have good chemical and thermal stability and good stability with respect to electrical fields and electromagnetic radiation. Additionally, the liquid crystal materials should have a low viscosity and give rise to short response times, low threshold voltages and high contrast in cells.

Furthermore they should, at standard operating temperatures, i.e., in as wide a range as possible below and above room temperature, have a suitable mesophase, for example a nematic or cholesteric mesophase for the above-mentioned cells. Since liquid crystals as a rule are used as mixtures of a number of components, it is important for the components to be readily miscible with one another. Other properties such as electrical conductivity, dielectric anisotropy and optical anisotropy must meet various requirements, depending on the cell type and field of application. For example, materials for cells having a twisted nematic structure should exhibit positive dielectric anisotropy and low electrical conductivity.

Matrix liquid crystal displays, for example, comprising integrated nonlinear elements to switch individual pixels (matrix LCDs) ideally require media having large positive dielectric anisotropy, broad-range nematic phases, relatively low birefringence, very high resistivity, good UV and temperature stability and low vapor pressure.

Such matrix liquid crystal displays are known. Suitable nonlinear elements for individually switching the separate pixels include active elements (i.e. transistors), for example. Such an arrangement is referred to as an "active matrix", allowing for a distinction between two types:

1. MOS (metal oxide semiconductor) or other diodes on a silicon wafer as the substrate.
2. Thin-film transistors (TFT) on a glass sheet as the substrate.

The use of monocrystalline silicon as a substrate material limits the display size, since even modular assembly of separate subdisplays gives rise to problems at the joints.

In the more promising type 2, which is preferred, the electro-optical effect used is usually the TN effect. A distinction is made between two technologies: TFTs composed of compound semiconductors such as CdSe, or TFTs on the basis of polycrystalline or amorphous silicon. Work on the latter technology is being carried out worldwide with great intensity.

The TFT matrix is applied on the inside of the one glass sheet of the display, while the other glass sheet on its inside carries the transparent counter-electrode. Compared with the size of the pixel electrode, the TFT is very small and hardly interferes with the image. This technology can also be extended to full color capability pictorial representations, where a mosaic of red, green and blue filters is arranged in such a way that filter elements are located opposite switchable picture elements in a one-to-one arrangement.

The TFT displays usually function as TN cells comprising crossed polarizers in transmission and employ backlighting.

The term matrix LCDs in this context encompasses any matrix display comprising integrated nonlinear elements, i.e. in addition to the active matrix it also includes displays comprising passive elements such as varistors or diodes (MIM=metal-insulator-metal).

Matrix LCDs of this type are suitable, in particular, for TV applications (e.g. portable televisions) or for high information level displays for computer applications (laptop) and in motor vehicle or aircraft production. In addition to problems regarding angular dependence of contrast and switching times, matrix LCDs present difficulties owing to insufficiently high resistivity of the liquid crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 et seq., Paris; STROMER, M., Proc. Eurodisplay 84, September 1984: Design of Thin Film Transistors for Matrix Addressing of Television Liquid Crystal Displays, p. 145 et seq., Paris]. As the resistance decreases, the contrast of a matrix LCD display deteriorates, and the problem of "afterimage elimination" can arise. As the resistivity of the liquid crystal mixture generally decreases over the lifetime of a matrix LCD, owing to interaction with the interior surfaces of the display, a high (initial) resistance is very important to achieve acceptable service life. Particularly with low-voltage mixtures it has hitherto been impossible to achieve very high resistivities. Moreover, it is important for the resistivity to exhibit as low an increase as possible with increasing temperature and after thermal exposure and/or exposure to UV. A further particularly disadvantageous feature is the low-temperature properties of the prior art mixtures. It is desirable that no crystallization and/or smectic phases occur even at low temperatures and that viscosity temperature dependence be as small as possible. The prior art matrix LCDs therefore do not meet present-day requirements.

Therefore a great need is still present for matrix LCDs having very high resistivity and at the same time having a wide operating temperature range, short switching times even at low temperatures, and a low threshold voltage, which do not exhibit the drawbacks of the prior art or exhibit them only to a lesser extent.

For TN (Schadt-Helfrich) cells, media are desirable which permit the following advantages in these cells:

extended nematic phase domain (especially towards low temperatures)

switchability at extremely low temperatures (outdoor use, motor vehicles, avionics), increased resistance to UV radiation (extended lifetime), and low optical birefringence.

The media available from the prior art do not permit these advantages to be achieved while at the same time maintaining other parameters.

For supertwisted cells (STN), media are desirable which permit higher multiplexability and/or lower threshold voltages and/or wider nematic phase domains (especially at low temperatures). For this purpose, a further expansion of the available parameter space (clearing point, transition smectic-nematic or melting point, viscosity, dielectric parameters, elastic parameters) is urgently required.

It is an object of the invention to provide media especially for such matrix LCDs, TN or STN displays which do not exhibit the above-mentioned drawbacks or exhibit them only to a lesser extent, and preferably at the same time have very high resistivities and low threshold voltages. This object requires liquid-crystalline compounds having a high clearing point and low rotational viscosity.

We have found that this object can be achieved if the liquid-crystalline compounds according to the invention are employed.

The invention therefore relates to liquid-crystalline compounds of formula I,

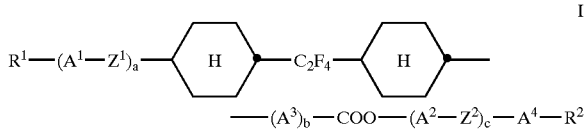

wherein $R^1$ is a straight-chain or branched alkyl radical having 1 to 15 C atoms which is unsubstituted, singly substituted by CN or $CF_3$, at least singly substituted by halogen, wherein optionally one or more $CH_2$ groups are substituted by —O—, —CO—, —S—, —CH═CH—, —C≡C—, —OC—O— or —O—CO— in such a way that O atoms are not directly linked together, $R^2$ is CN, $SF_5$, H, F, Cl, NCS, SCN, or a straight-chain or branched alkyl radical having 1 to 15 C atoms which is unsubstituted, singly substituted by CN or $CF_3$, at least singly substituted by halogen, wherein optionally one or more $CH_2$ groups are substituted by —O—, —CO—, —S—, —CH═CH—, —C≡C—, —OC—O— or —O—CO— in such a way that O atoms are not directly linked together, $A^1$, $A^2$, $A^3$ and $A^4$ are each, independently, a 1,4-cyclohexenylene radical in which one or two non-adjacent $CH_2$ groups are optionally replaced by —O— or —S—, a 1,4-phenylene radical in which one or two CH groups are optionally replaced by N, or a radical selected from piperidine-1,4-diyl, 1,4-bicyclo[2.2.2]octylene, naphthalene-2,6-diyl, decahydronaphthalene-2,6-diyl, and 1,2,3,4-tetrahydronaphthalene-2,6-diyl, wherein each is optionally singly substituted or polysubstituted by halogen, $Z^1$ and $Z^2$ are each, independently, —CO—O—, —O—CO—, —$CF_2$O—, —O$CF_2$—, —$CH_2$O—, —O$CH_2$—, —$CH_2CH_2$—, —$(CH_2)_4$—, —$C_2F_4$—, —$CF_2CH_2$—, —$CH_2CF_2$—, —CF═CF—, —CH═CH—, —C≡C— or a single bond, a is 0, 1 or 2, b is 0, 1 or 2, and c is 0, 1 or 2, wherein a+b+c≦2.

The invention further relates to the use of the compounds of formula I in liquid-crystalline media.

The compounds of formula I have a wide application range. Depending on the choice of substituents, these compounds can serve as base materials for liquid-crystalline media. Alternatively, compounds of the formula I can also be admixed to liquid-crystalline base materials from other classes of compounds, for example, in order to influence the dielectric and/or optical anisotropy of such a dielectric and/or to optimise its threshold voltage and/or its viscosity.

The compounds of formula I are colorless in their pure state and form liquid-crystalline mesophases in a temperature range favorable for electro-optical use. In particular, the compounds according to the invention are distinguished by their high clearing point and their low rotational viscosity values. They are stable chemically, thermally, and with respect to light.

The invention particularly relates to compounds of formula I, where $R^1$ is alkyl having from 1 to 10 C atoms, or an alkenyl radical having from 2 to 10 C atoms.

Preferred are compounds of formula I where c is 0. $Z^1$ and $Z^2$ are preferably a single bond, or alternatively —$CF_2$O—, —O$CF_2$—, —$C_2F_4$—, —$CH_2$O—, —O$CH_2$— or —COO—. Preferably a is 0.

If $R^1$ and/or $R^2$ is an alkyl radical and/or an alkoxy radical, this can be straight-chain or branched. Preferably it is straight-chain, has 2, 3, 4, 5, 6 or 7 C atoms, and therefore preferably is ethyl, propyl, butyl, pentyl, hexyl, heptyl, ethoxy, propoxy, butoxy, pentoxy, hexoxy, heptoxy, methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl preferably is straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and/or $R^2$ is an alkenyl radical, it can be straight-chain or branched. Preferably it is straight-chain and has from 2 to 10 C atoms. It is therefore, in particular, vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5-, or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

If $R^1$ and/or $R^2$ is an alkyl radical, in which one $CH_2$ group has been replaced by —O— and one by —CO—, these are preferably adjacent. These therefore comprise an acyloxy group —CO—O— or an oxycarbonyl group —O—CO—. Preferably, they are straight-chain and have from 2 to 6 C atoms.

In particular, they therefore are acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, or 4-(methoxycarbonyl)butyl.

If $R^1$ and/or $R^2$ is an alkyl or alkenyl radical singly substituted by CN or $CF_3$, said radical is preferably straight-chain. The substitution by CN or $CF_3$ can be in any position.

If $R^1$ and/or $R^2$ is an alkyl or alkenyl radical at least singly substituted by halogen, said radical is preferably straight-chain and halogen is preferably F or Cl. In the case of polysubstitution, halogen is preferably F. The resulting radicals also include perfluorinated radicals. In the case of single substitution, the fluoro or chlorine substituent can be in any position, but preferably in the ω-position.

Compounds of formula I carrying branched pendant groups $R^1$ and/or $R^2$ are occasionally of interest because of their better solubility in the conventional liquid-crystalline base materials. In particular, however, they are of interest as chiral dopants if they are optically active. Smectic compounds of this type are suitable as components for ferroelectric materials.

Compounds of formula I having $S_A$ phases are suitable, for example, for thermally addressed displays.

Branched groups of this type as a rule do not contain more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy.

$R^2$ is preferably H, F, Cl, CN, $CF_3$, $SF_5$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2H$, $OCF_2CF_2H$, $OCF_2CF_2H$, $OCFHCF_2CF_3$, $OCFHCF_2CF_2H$, $OCFHCFHCF_3$, $OCH_2CF_2CF_3$, $OCF_2CF_2CF_3$, $OCF_2CFHCFH_2$, $OCF_2CH_2CF_2H$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH_3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCHCH_2CH_3$, $OCH_2CFHCH_3$, $OCH_2CH_2CF_2H$, $OCCl_2CF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCFHCCl_2CF_3$, $OCCl_2CF_2CFH_2$, $OCH_2CF_2CCl_2F$, $OCCl_2CFHCF_2H$, $OCClHCClFCF_2H$, $OCF_2CClHCClH_2$, $OCF_2CH_2CCl_2H$, $OCClFCFHCH_3$, $OCF_2CClFCCl_2H$, $OCClFCH_2CFH_2$, $OCFHCCl_2CFH_2$, $OCCl_2CF_2CH_3$, $OCH_2CF_2CClH_2$, $OCCl_2CFHCFH_2$, $OCH_2CClFCFCl_2$, $OCH_2CH_2CF_2H$, $OCClHCClHCF_2H$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $CF=CF_2$, $OCH=CF_2$, $OCF=CF_2$, $CH=CHF$, $OCH=CHF$, $CF=CHF$, $OCF=CHF$, especially F, Cl, CN, $CF_3$, $SF_5$, $CF_2H$, $OCF_3$, $OCF_2H$, $OCFHCF_3$, $OCFHCFH_2$, $OCFHCF_2H$; $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCF_2CF_2CF_3$, $OCF_2CHFCF_3$, $OCClFCF_2CF_3$.

For the sake of simplicity, hereinafter Cyc represents a 1,4-cyclohexylene radical, Che a 1,4-cyclohexenyl radical, Dio a 1,3-dioxane-2,5-diyl radical, Dit a 1,3-dithiane-2,5-diyl radical, Phe a 1,4-phenylene radical, Pyd a pyridine-2,5-diyl radical, Pyr a pyrimidine-2,5-diyl radical, Bi a bicyclo [2.2.2]octylene radical, PheF a 2- or 3-fluoro-1,4-phenylene radical, PheFF a 2,3-difluoro- or 2,6-difluoro-1,4-phenylene radical, Nap a substituted or unsubstituted naphthalene radical, Dec a decahydronaphthalene radical.

The compounds of the formula I accordingly comprise the preferred compounds having three rings of the subformulae Ia to If:

| | |
|---|---|
| $R^1$-Cyc-$C_2F_4$-Cyc-COO-Phe-$R^2$ | Ia |
| $R^1$-Cyc-$C_2F_4$-Cyc-COO-PheF-$R^2$ | Ib |
| $R^1$-Cyc-$C_2F_4$-Cyc-COO-PheFF-$R^2$ | Ic |
| $R^1$-Cyc-$C_2F_4$-Cyc-COO-Bi-$R^2$ | Id |
| $R^1$-Cyc-$C_2F_4$-Cyc-COO-Nap-$R^2$ | Ie |
| $R^1$-Cyc-$C_2F_4$-Cyc-COO-Dec-$R^2$ | If |

Compounds having four rings of the subformulae Ik to Iw:

| | |
|---|---|
| $R^1$-Cyc-$C_2F_4$-Cyc-Cyc-COO-Phe-$R^2$ | Ik |
| $R^1$-Cyc-$C_2F_4$-Cyc-Cyc-COO-PheF-$R^2$ | Il |
| $R^1$-Cyc-$C_2F_4$-Cyc-Cyc-COO-PheFF-$R^2$ | Im |
| $R^1$-Cyc-$C_2F_4$-Cyc-Cyc-COO-Nap-$R^2$ | In |
| $R^1$-Cyc-$C_2F_4$-Cyc-Cyc-COO-Dec-$R^2$ | Io |
| $R^1$-Cyc-$C_2F_4$-Cyc-Cyc-COO-Bi-$R^2$ | Ip |
| $R^1$-Cyc-$C_2F_4$-Cyc-Phe-COO-Phe-$R^2$ | Iq |
| $R^1$-Cyc-$C_2F_4$-Cyc-Phe-COO-PheF-$R^2$ | Ir |
| $R^1$-Cyc-$C_2F_4$-Cyc-Phe-COO-PheFF-$R^2$ | Is |
| $R^1$-Cyc-$C_2F_4$-Cyc-PheF-COO-Phe-$R^2$ | It |
| $R^1$-Cyc-$C_2F_4$-Cyc-PheFF-COO-Phe-$R^2$ | Iu |
| $R^1$-Cyc-$C_2F_4$-Cyc-PheFF-COO-PheFF-$R^2$ | Iv |
| $R^1$-Cyc-$C_2F_4$-Cyc-COO-Phe-Cyc-$R^2$ | Iw |

Particularly preferred among these are the compounds of the subformulae Ia, Ib and Ic.

In the compounds of the previous and following formulae, $R^2$ is preferably F, CN, $OCF_3$, $OCHF_2$, $CF_3$, $OCHFCF_3$, $OC_2F_5$ or $OCF_2CHFCF_3$, straight-chain alkyl or alkoxy.

$R^1$ is preferably straight-chain, unsubstituted alkyl, alkoxy, alkenyloxy or alkenyl having up to 10 C atoms.

$A^2$ is preferably Phe, PheF, PheFF, Cyc or Che, also Pyr or Dio, Dec or Nap. Preferably the compounds of formula I do not include more than one of the radicals Bi, Pyd, Pyr, Dio, Dit, Nap or Dec.

Preferred are compounds of formula I in which $A^1$ is a singly or doubly substituted 1,4-phenylene. In particular, these are 2-fluoro-1,4-phenylene, 3-fluoro-1,4-phenylene, 2,3-difluoro-1,4-phenylene and 2,6-difluoro-1,4-phenylene.

Preferred smaller groups of compounds of formula I are those of the subformulae I1 to I24:

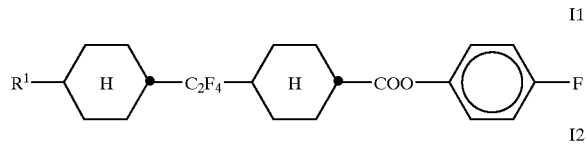

I1

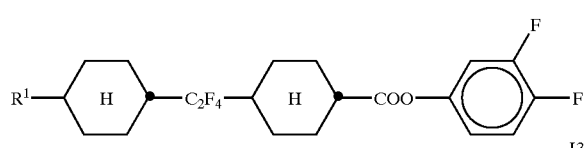

I2

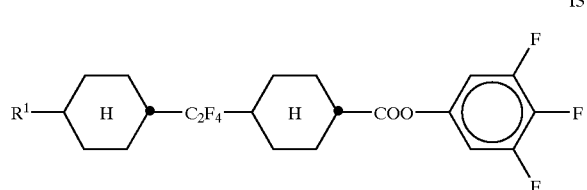

I3

I4
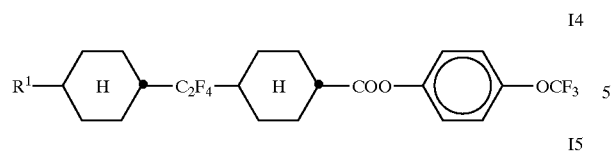
I5
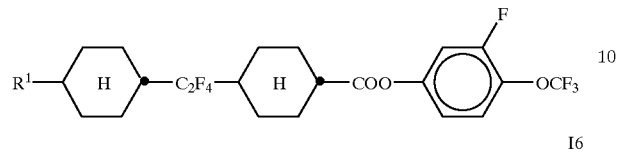
I6
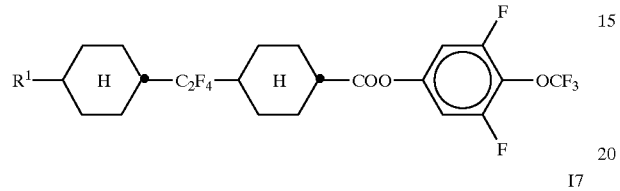
I7
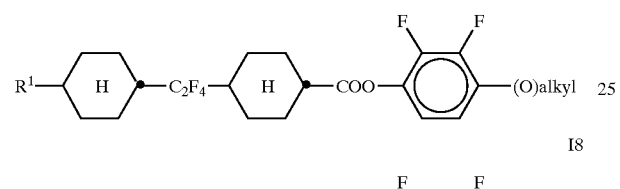
I8
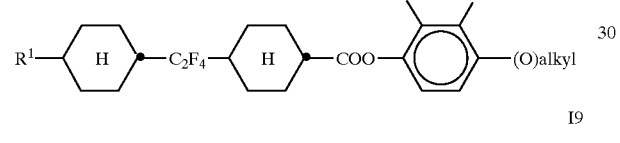
I9
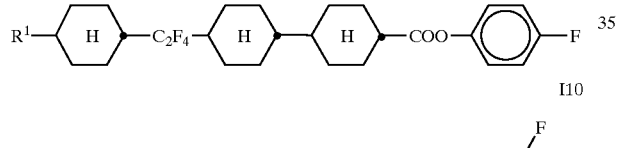
I10
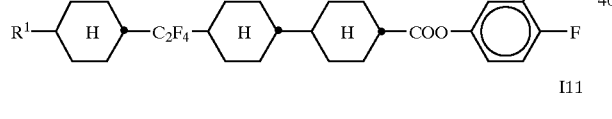
I11
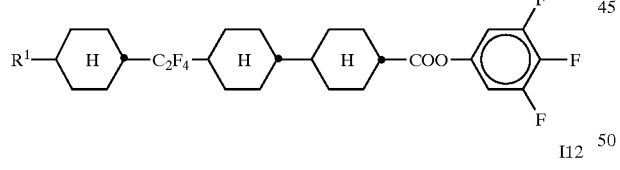
I12
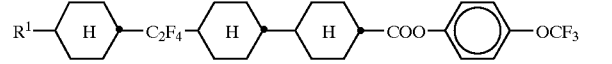
I13
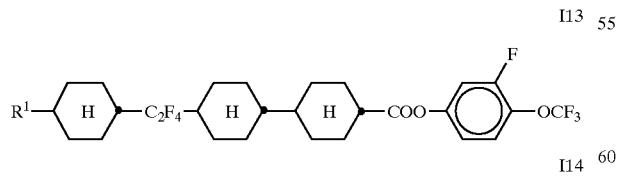
I14
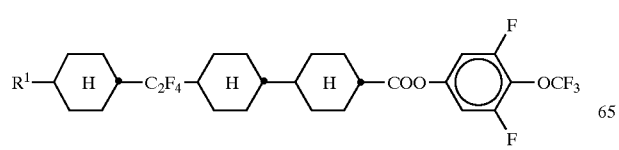
I15
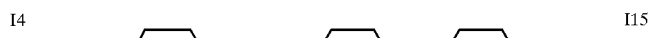
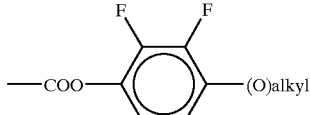
I16
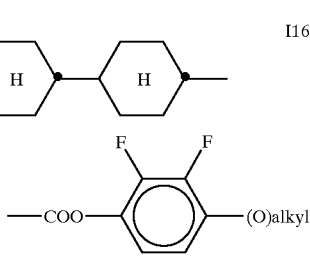
I17
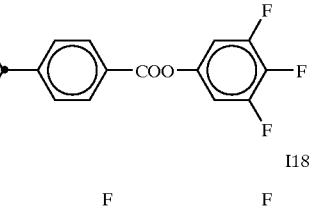
I18
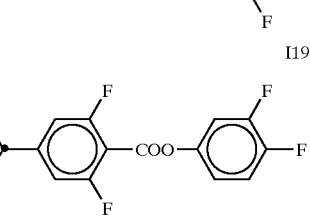
I19
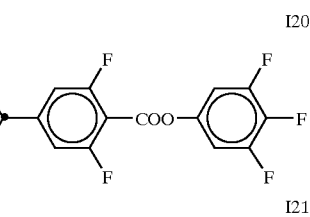
I20
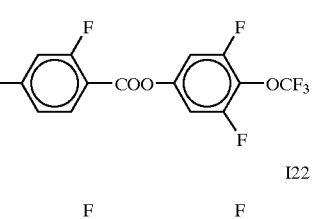
I21
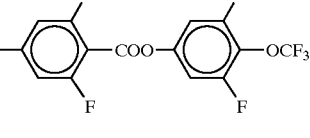
I22

-continued

I23: R$^1$—[H]—C$_2$F$_4$—[H]—COO—[phenyl]—[H]—R$^2$

I24: R$^1$—[H]—C$_2$F$_4$—[H]—COO—[phenyl]—SF$_5$ where

R$^1$ has the meanings described previously and "alkyl" is a straight-chain or branched alkyl having 1–9 C atoms.

The compounds of the formula I are prepared in accordance with methods known per se, as described in the literature (e.g. in the standard textbooks such as Houben-Weyl, Methoden der Organischen Chemie, Georg-Thieme-Verlag, Stuttgart) specifically under reaction conditions known and suitable for these reactions. Variants known per se but not mentioned here in detail are also included.

The compounds according to the invention can, for example, be prepared as follows:

Scheme 1

(R' is alkyl; L$^1$ and L$^2$ are each, independently, H or R)

HO—[phenyl]—CF$_2$CF$_2$—[phenyl]—OH $\xrightarrow{\text{hydrogenation}}_{\text{H}_2,\text{ Rh—C}}$ HO—[cyclohexyl]—C$_2$F$_4$—[cyclohexyl]—OH $\xrightarrow{\text{PCC}}_{\text{CH}_2\text{Cl}_2}$ O=[cyclohexyl]—C$_2$F$_4$—[cyclohexyl]=O $\xrightarrow{\text{HO—C(CH}_3)_2\text{—OH}}_{\text{cat. H}_2\text{SO}_4}$ O=[cyclohexyl]—C$_2$F$_4$—[cyclohexyl-dioxaspiro(dimethyl)] $\xrightarrow{(C_nH_{2n+1})CH_2PPh_3{}^+Br^-}_{\text{KO}^t\text{Bu, THF}}$ C$_n$H$_{2n+1}$=[cyclohexyl]—C$_2$F$_4$—[cyclohexyl-dioxaspiro(dimethyl)] $\xrightarrow{\text{hydrogenation}}_{\text{H}_2,\text{ Pd—C}}$ C$_n$H$_{2n+1}$—CH$_2$—[cyclohexyl]—C$_2$F$_4$—[cyclohexyl-dioxaspiro(dimethyl)] $\xrightarrow{\text{HCOOH}}_{\text{toluene}}$ C$_n$H$_{2n+1}$—CH$_2$—[cyclohexyl]—C$_2$F$_4$—[cyclohexyl]=O $\xrightarrow{\text{R'CH}_2\text{PPh}_3{}^+\text{Br}^-}_{\text{KO}^t\text{Bu, THF}}$ C$_n$H$_{2n+1}$—CH$_2$—[cyclohexyl]—C$_2$F$_4$—[cyclohexyl]=CH—OMe $\xrightarrow[2.\text{ MeOH, cat. NaOH}]{1.\text{ HCOOH, toluene}}$ C$_n$H$_{2n+1}$—CH$_2$—[cyclohexyl]—C$_2$F$_4$—[cyclohexyl]—CHO $\xrightarrow{\text{CrO}_3}_{\text{H}_2\text{SO}_4,\text{ acetone}}$ C$_n$H$_{2n+1}$—CH$_2$—[cyclohexyl]—C$_2$F$_4$—[cyclohexyl]—COOH $\xrightarrow{\text{HO—[phenyl(L}^1,\text{L}^2)]—R^2}_{\text{DCC, toluene; DMAP}}$ C$_n$H$_{2n+1}$—CH$_2$—[cyclohexyl]—C$_2$F$_4$—[cyclohexyl]—COO—[phenyl(L$^1$,L$^2$)]—R$^2$ The invention also relates to electro-optical displays (in particular STN displays or matrix LCDs with two plane-parallel substrates which, together with a border, form a cell, which have integrated nonlinear elements for switching individual pixels on the substrates and, wherein a nematic liquid crystal mixture having positive dielectric anisotropy and high resistivity is present in the cell) which comprise media as described previously and to the use of these media for electro-optical purposes.

The liquid crystal mixtures according to the invention permit considerable expansion of the available parameter space.

The media according to the invention achieve combinations of clearing point, optical anisotropy, viscosity at low temperature, thermal and UV stability and dielectric anisotropy far superior to current prior art materials.

So far it has not been possible to adequately meet the requirements of a high clearing point, a nematic phase at low temperature and a high Δε. While liquid-crystal mixtures such as e.g. MLC-6476 and MLC-6625 (Merck KGaA, Darmstadt, Germany) do exhibit comparable clearing points and low temperature stabilities, they have relatively high Δn values as well as higher threshold voltages of about ≧1.7 V.

Other mixture systems have comparable viscosities and values of Δε, but have clearing points around 60° C.

The liquid crystal mixtures according to the invention, while maintaining the nematic phase down to −20° C., preferably down to −30° C., and particularly preferably down to −40° C., make it possible to achieve clearing points above 80° C., preferably above 90° C., and particularly preferably above 100° C., with simultaneous dielectric anisotropy values of Δε≧4, and preferably ≧6 and a high specific resistivity, which makes possible excellent STN displays and matrix LCDs. The mixtures in particular are characterized by low operating voltages. The TN thresholds are below 1.5 V, preferably below 1.3 V.

It follows that with suitable choices for the components of the mixtures according to the invention one can achieve higher clearing points (e.g. above 110° C.) in conjunction with a higher threshold voltage, or lower clearing points in conjunction with lower threshold voltages while maintaining other advantageous properties. It is equally possible, in conjunction with a correspondingly small increase in viscosities, to obtain mixtures with a larger Δε and consequently lower thresholds. The matrix LCDs according to the invention preferably operate in the first transmission minimum according to Gooch and Tarry [C. H. Gooch and H. A. Tarry, Electron. Lett. 10, 2–4, 1974; C. H. Gooch and H. A. Tarry, Appl. Phys. Vol. 8, 1575–1584, 1975], resulting not only in particularly favorable electro-optical properties such as e.g. steep slope of the characteristic curve and low angular dependence of contrast (DE-C 3022818), but also a smaller dielectric anisotropy being sufficient in the second minimum in conjunction with a threshold voltage equal to that of an analogue display. Consequently it is possible, using the mixtures according to the invention, to achieve distinctly higher resistivities in the first minimum than with mixtures comprising cyano compounds. Those skilled in the art, using simple routine methods, are able, via a suitable choice of the individual components and their proportions by weight, to adjust the birefringence required for a predefined layer thickness of the matrix LCD.

The flow viscosity $v_{20}$ at 20° C. is preferably <60 mm²·s⁻1, particularly preferably <50 mm²·s⁻¹. The nematic phase domain is preferably at least 90°, in particular at least 100°. Preferably, this domain extends at least from −30° to +80°.

Measurements of the "capacity holding ratio" (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a distinctly smaller decrease in HR with increasing temperature than analogous mixtures comprising, instead of the compounds of the formula I, cyanophenylcyclohexanes of the formula

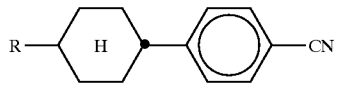

or esters of the formula

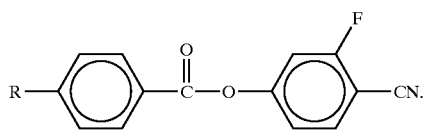

The UV stability of the mixtures according to the invention is likewise considerably better, i.e. they exhibit a distinctly smaller decrease in HR under exposure to UV.

Preferably, the media according to the invention are based on a plurality of (preferably two, three, four or more) compounds of formula I, i.e. the proportion of these compounds is 5–95%, preferably 10–60% and particularly preferably in the range of 15–40%.

Individual compounds of the formulae I to X (formulae II to X are described below) and their subformulae which can be used in the media according to the invention are either known or can be prepared in a manner similar to that of known compounds.

Preferred embodiments are specified below:

The medium preferably comprises 1, 2 or 3 homologous compounds of formula I, no more than 10% of each homologue being present in the mixture.

The medium comprises compounds of formula I where $R^1$ is preferably ethyl and/or propyl, alternatively butyl, pentyl, hexyl and heptyl. Compounds of formula I having short side chains $R^1$ have a positive effect on the elastic constants, especially $K_1$, and result in mixtures having particularly low threshold voltages.

The medium additionally comprises one or more compounds of formulae II to X:

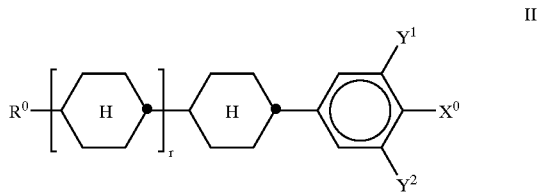

II

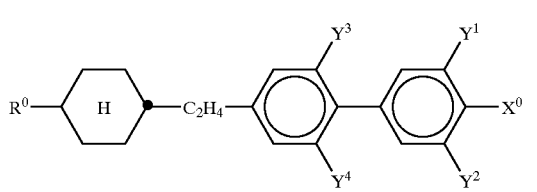

III

-continued

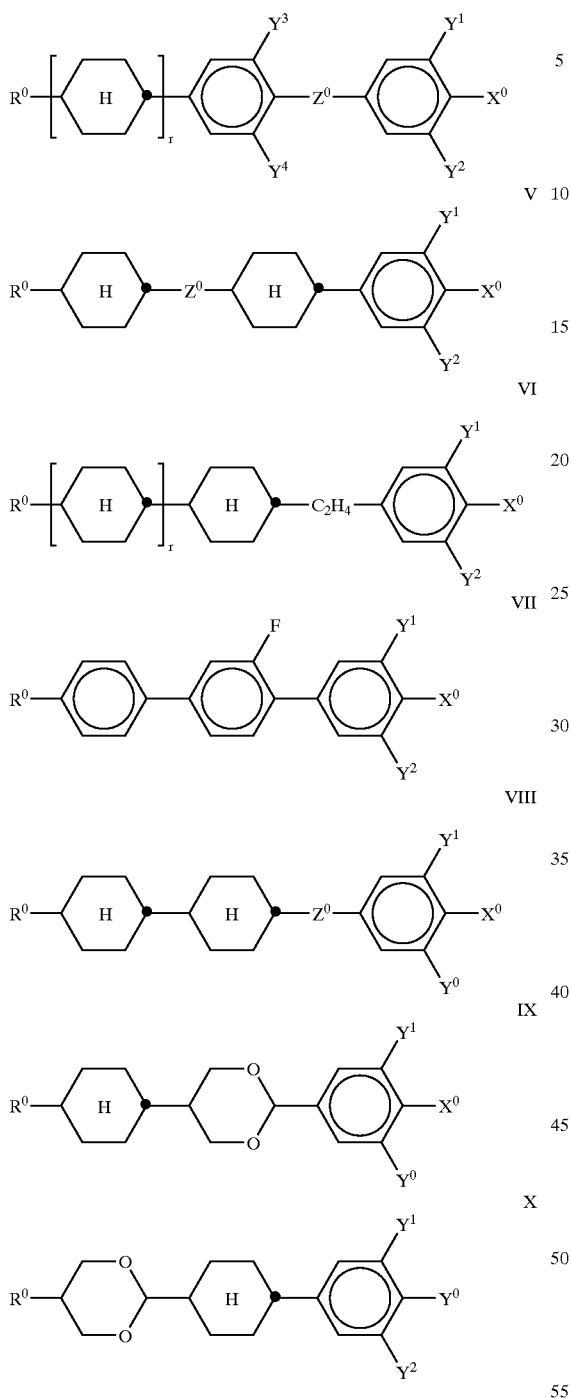

where the individual radicals have the following meanings:
$R^0$ is n-alkyl; oxaalkyl, fluoroalkyl, alkenyloxy or alkenyl, each having up to 9 C atoms,
$X^0$ is halogenated alkyl, halogenated alkenyl, halogenated alkenyloxy, halogenated alkoxy, each having up to 7 C atoms, F or Cl,
$Z^0$ is —CH=CH—, —C$_2$H$_4$—, —C$_2$F$_4$—, —CF=CF—, —CF$_2$O—, —OCF$_2$— or —COO—,
$Y^1, Y^2, Y^3$ and $Y^4$ are, each independently, H or F, and
r is 0 or 1.

The compound of formula IV is preferably

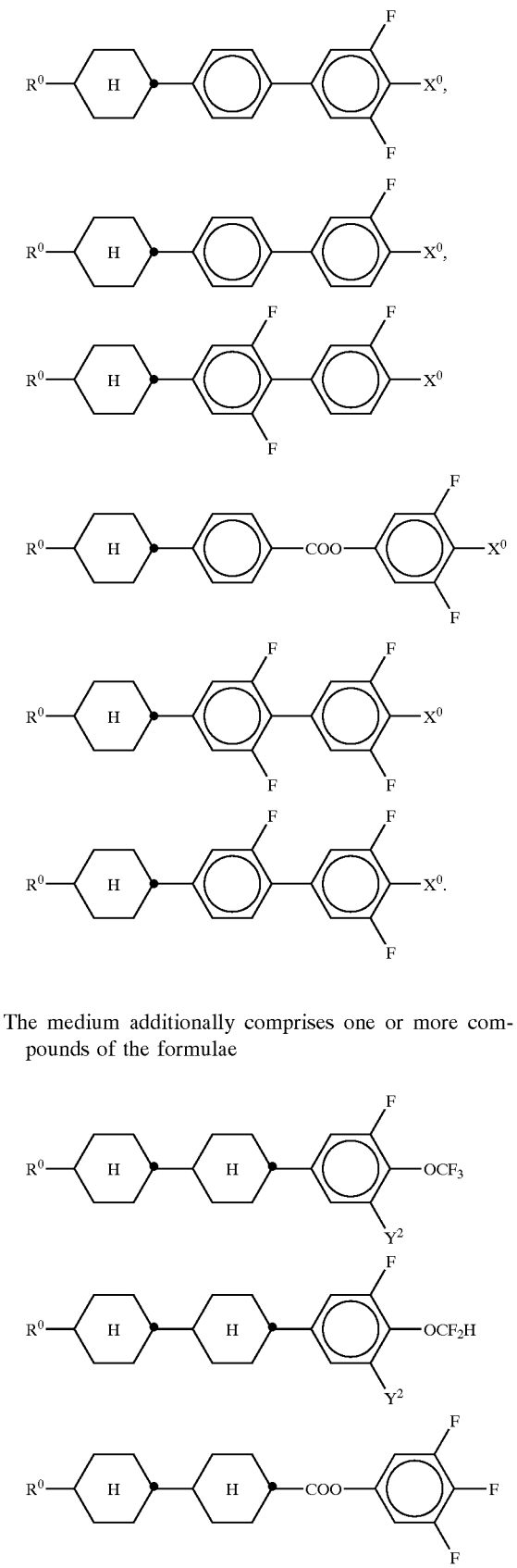

The medium additionally comprises one or more compounds of the formulae

-continued
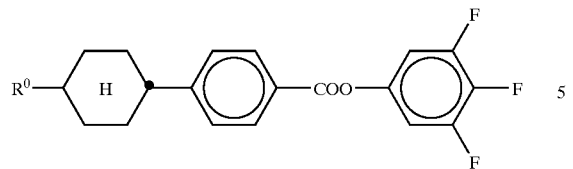
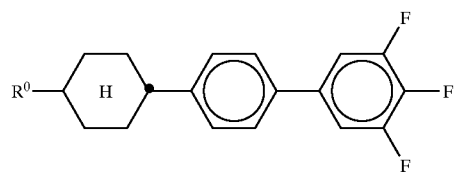
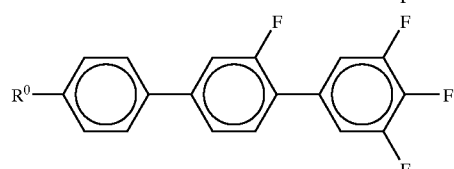
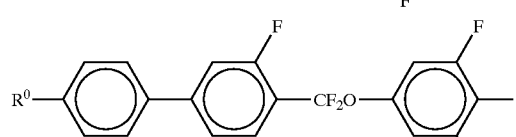
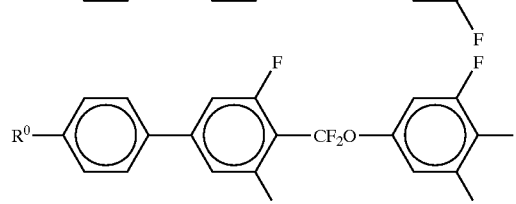
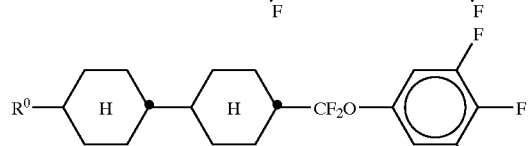
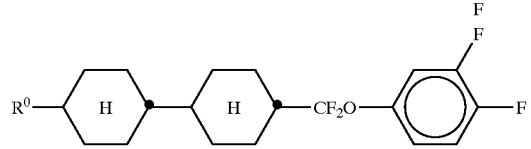
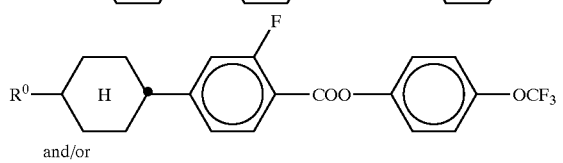
and/or
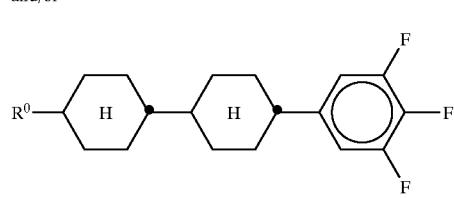
wherein $R^0$ and $Y^2$ are as previously defined.
The medium preferably comprises one, two or three, alternatively four homologues of the compounds of H1 to H17 (n=1–7):
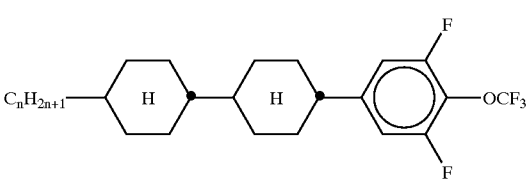

-continued

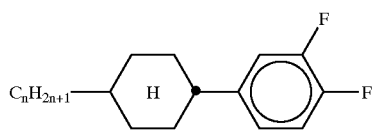
H10

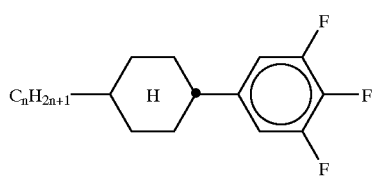
H11

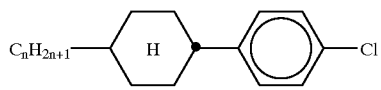
H12

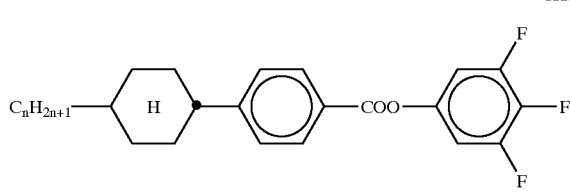
H13

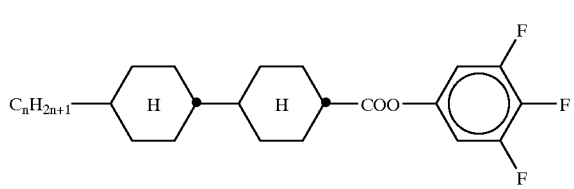
H14

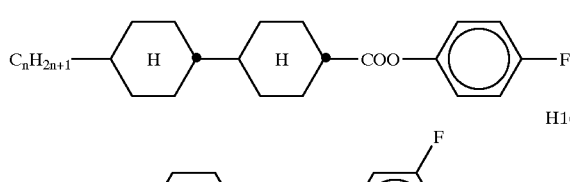
H15

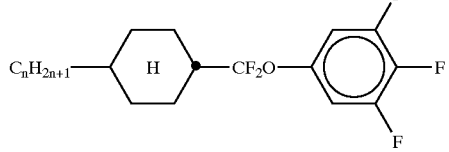
H16

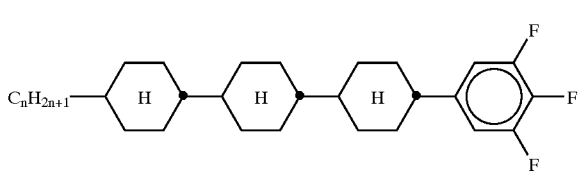
H17

The medium additionally comprises one or more dioxanes of the formula DI and/or DII,

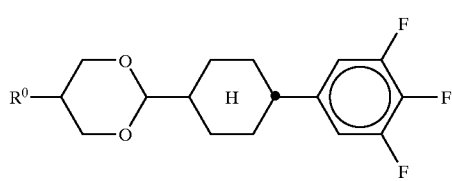
DI

-continued

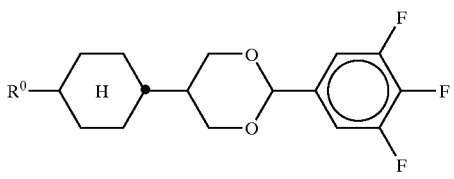
DII wherein $R^0$ is n-alkyl, oxaalkyl, fluoroalkyl, alkenyloxy or alkenyl, each having up to 9 C atoms. Preferably $R^0$ in the compounds of formula DI and/or DII is straight-chain alkyl or alkenyl having up to 7 C atoms.

The medium additionally comprises one or more compounds of formulae XI to XVI:

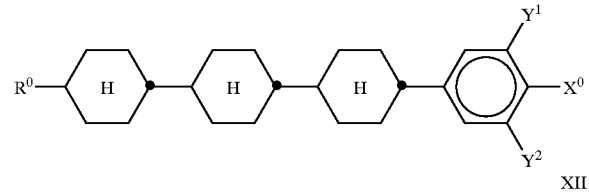
XI

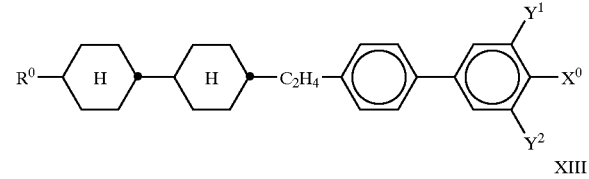
XII

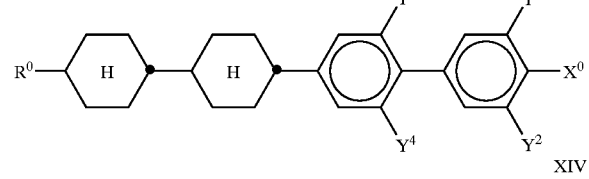
XIII

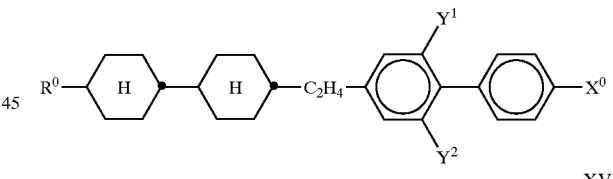
XIV

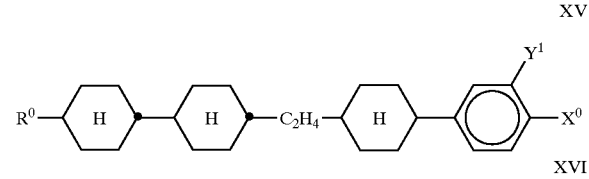
XV

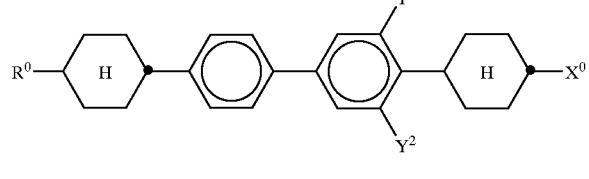
XVI wherein $R^0$ is n-alkyl, oxaalkyl, fluoroalkyl, alkenyloxy or alkenyl, each having up to 9 C atoms. $X^0$ is F, Cl, halogenated alkyl, hologenated alkenyl, halogenated alkenyloxy or halogenated alkoxy having up to 7 C atoms. $Y^1$, $Y^2$, $Y^3$ and $Y^4$ are, each independently, H or F. $X^0$ preferably is F, Cl, $CF_3$, $OCF_3$, $OCHF_2$. $R^0$ preferably is alkyl, oxaalkyl, fluoroalkyl, alkenyl or alkenyloxy.

The proportion of compounds of formulae I to X together in the overall mixture is at least 50 wt %.

The proportion of compounds of formula I in the overall mixture is from 5 to 50 wt %.

The proportion of compounds of formulae II to X in the overall mixture is from 30 to 70 wt %.

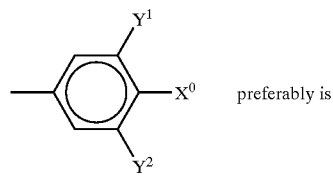 preferably is

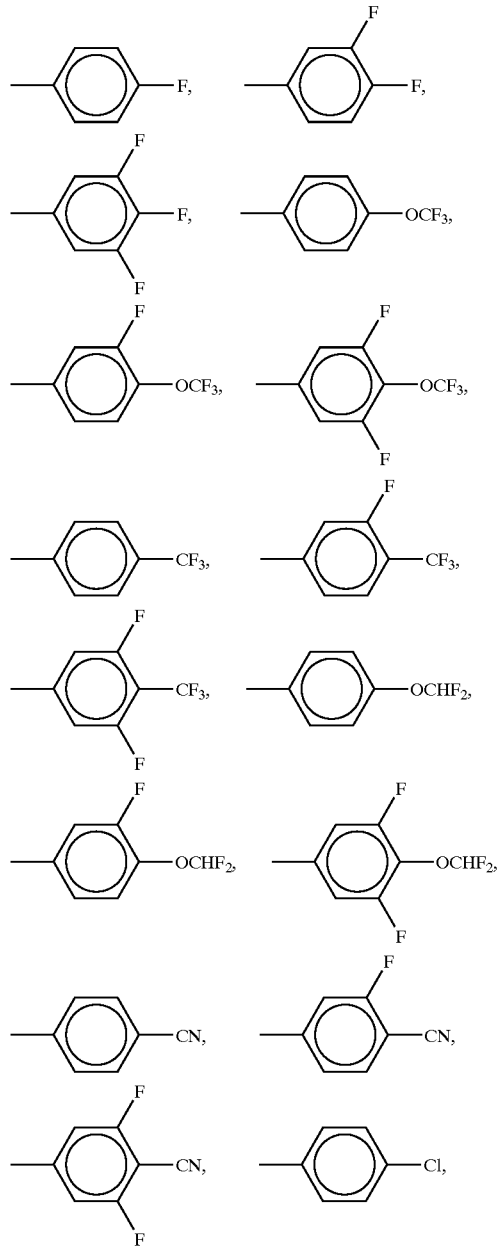

-continued

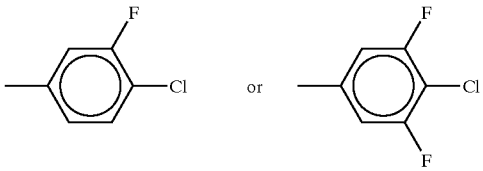

The medium comprises compounds of formulae II, III, IV, V, VI, VII, VIII, IX and/or X.

$R^0$ is straight-chain alkyl or alkenyl of 2 to 7 C atoms.

The medium essentially comprises compounds of the formulae II to XVI.

The medium comprises further compounds, preferably of formulae XVII to XX:

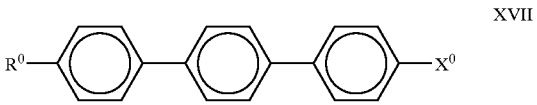

XVII

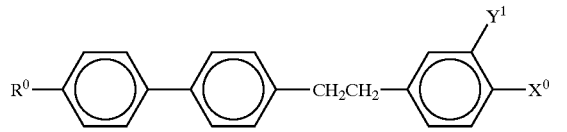

XVIII

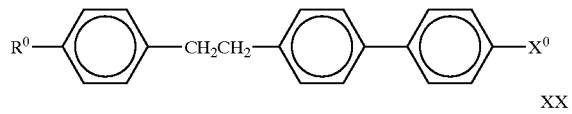

XIX

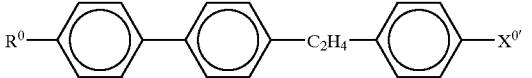

XX ($X^{0'}$ = F or Cl)

wherein $R^0$ and $X^0$ are as previously defined and the 1,4-phenylene rings can be CN-, chloro- or fluorosubstituted. Preferably, the 1,4-phenylene rings are singly substituted or polysubstituted by fluorine atoms.

The medium comprises further compounds, preferably of formulae RI to RX,

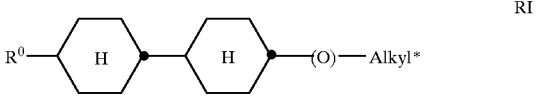

RI

RII

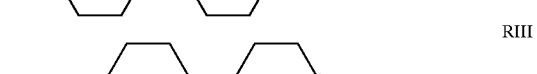

RIII

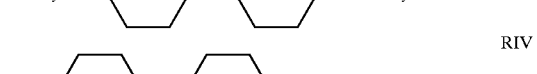

RIV

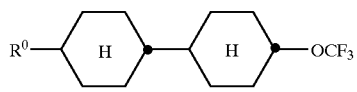
RV

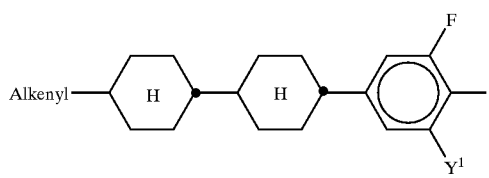
RVI

RVII

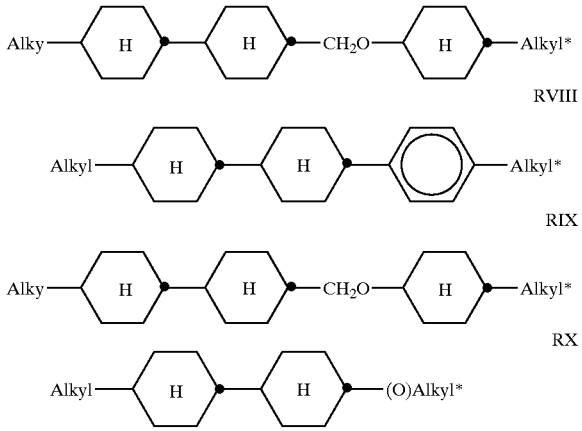

RVIII

RIX

RX wherein

R⁰ is n-alkyl, oxaalkyl, fluoroalkyl, alkenyloxy or alkenyl each having up to 9 C atoms, d is 0, 1 or 2, $Y^1$ is H or F, Alkyl or Alkyl* are, each independently, a straight-chain or branched alkyl radical having 1–9 C atoms, Alkenyl or Alkenyl* are, each independently, a straight-chain or branched alkenyl radical having up to 9 C atoms.

The medium preferably comprises one or more compounds of the formulae

RIa

RIb

RIIa

RIIb

RIIIa

RIIIb

RIIIc

RIVa wherein n and m are each an integer of 1 to 9.

The proportion by weight of compounds of formula I: compounds of formulas (II+IIII+IV+V+VI+VII+VIII+IX+X) together is preferably from 1:10 to 10:1.

The medium essentially comprises compounds of formulae I to XVI.

It was found that even a relatively small proportion of the compounds of formula I mixed with conventional liquid crystal materials, but in particular with one or more compounds of formula II, III, IV, V, VI, VII, VIII, IX and/or X leads to a considerable decrease in the threshold voltage and to low values of the birefringence, wide-domain nematic phases with low smecticnematic transition: temperatures, thereby improving the storage stability. The compounds of the formulae I to X are colorless, stable and readily miscible with one another and with other liquid crystal materials.

The term "alkyl" or "alkyl" encompasses straight-chain and branched alkyl groups having 1–9 carbon atoms, particularly the straight-chain groups methyl, ethyl, propyl, butyl, pentyl, hexyl and heptyl. Groups having 2–5 carbon atoms are preferred.

The term "alkenyl" or "alkenyl" encompasses straight-chain and branched alkenyl groups having up to 9 carbon atoms, preferably the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, especially preferred are $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are preferred.

The term "fluoroalkyl" preferably comprises straight-chain groups with terminal fluorine, i.e., fluoromethyl, 2-fluoroethyl, 3-fluoropropyl, 4-fluorobutyl, 5-fluoropentyl, 6-fluorohexyl and 7-fluoroheptyl. Other positions of fluorine are not precluded, however.

The term "oxaalkyl" preferably comprises straight-chain radicals of the formula $C_nH_{2n+1}$—O—$(CH_2)_m$, where n and m each, independently of one another, are 1 to 6. Preferably, n is 1 and m is 1 to 6.

By varying the choice for $R^0$ and $X^0$, one can modify the response times, the threshold voltage, the slope of the transmission characteristics etc. as desired. For example, 1E-alkenyl radicals, 3E-alkenyl radicals, 2E-alkenyloxy radicals and the like as a rule lead to shorter response times, improved nematic tendencies and a higher ratio of the elastic constants $k_{33}$ (bend) and $k_{11}$ (splay), compared with alkyl or alkoxy radicals. 4-Alkenyl radicals, 3-alkenyl radicals and the like generally result in lower threshold voltages and smaller values of $k_{33}/k_{11}$ than alkyl and alkoxy radicals.

A —$CH_2CH_2$— group in $Z^1$ generally leads to higher values of $k_{33}/k_{11}$, compared to a single covalent bond.

Higher values of $k_{33}/k_{11}$ permit, for example, less steep transmission characteristics in TN cells with twists of 90° (to achieve grey hues) and steeper transmission characteristics in STN, SBE and OMI cells (higher multiplexability) and vice versa.

The optimal quantitative ratio of the compounds of the formula I to formulae II+III+IV+V+VI+VII+VIII+IX+X largely depends on the desired characteristics, on the choice of components for the formulae I, II, III, IV, V, VI, VII, VIII, IX and/or X and on the choice of any further components. Suitable quantitative ratios within the above-specified range can readily be determined ad hoc.

The total quantity of compounds of the formulae I to XVI in the mixtures according to the invention is not critical. The mixtures can therefore comprise one or more further components, to optimize various properties. The observed effect on the response times and on the threshold voltage, however, is as a rule higher, the higher the overall concentration of compounds of the formulae I to XVI.

In a preferred embodiment, the media according to the invention comprise compounds of the formulae II to X (preferably II and/or III), where $X^0$ is $OCF_3$, $OCHF_2$, F, $OCH=CF_2$, $OCF=CF_2$, $OCF_2CHFCF_3$ or $OCF_2-CF_2H$. A beneficial synergistic effect with the compounds of formula I results in particularly advantageous properties.

The mixtures according to the invention having low optical anisotropy ($\Delta n<0.07$) are particularly suitable for reflective displays. Low $V_{th}$ mixtures are especially suitable for 3.3 V drivers and also for 4 V or 5 V drivers. Mixtures free from esters are preferred for the latter applications.

In the present application and in the following examples, the construction of the matrix LCD according to the invention comprising polarizers, electrode baseplates and electrodes with a surface treatment corresponds to the standard design of such displays. Within the present context, the term "standard design" is comprehensive and additionally covers any variations and modifications of the matrix LCD, including in particular matrix display elements on the basis of poly-Si TFT or MIM.

An essential difference between the displays according to the invention and the current customary displays based on the twisted nematic cell is the choice of liquid crystal parameters of the liquid crystal layer.

The preparation of the liquid crystal mixtures which can be used according to the invention is carried out by methods which are customary per se. As a rule, the desired quantity of the components used in smaller amounts is dissolved in the component which constitutes the main ingredient, preferably at an elevated temperature. An alternative procedure is to mix solutions of the components in an organic solvent, e.g. in acetone, chloroform or methanol, and then, after thorough mixing, to remove the solvent again, for example by distillation.

The dielectrics can also comprise further additives known to those skilled in the art and described in the literature. For example, 0–15% of pleochroic dyes or chiral dopants can be added.

C refers to a crystalline phase, S to a smectic phase, $S_c$ to a smectic phase, N to a nematic phase and I to the isotropic phase.

$V_{10}$ denotes the voltage for 10% transmission (viewing direction perpendicular to the substrate surface). $t_{on}$ denotes the on and $t_{off}$ the off time at an operating voltage corresponding to 2.0 times the value of $V_{10}$. $\Delta n$ denotes the optical anisotropy and $n_0$ the refractive index. $\Delta\epsilon$ denotes the dielectric anisotropy ($\Delta\epsilon=\epsilon_\parallel-\epsilon_\perp$, where $\epsilon_\parallel$ refers to the dielectric constant parallel to the longitudinal axes of the molecule and $\epsilon_\perp$ is the dielectric constant perpendicular thereto). The electro-optical data were measured in a TN cell in the 1st minimum (i.e. at a d·$\Delta n$ value of 0.5) at 20° C., unless explicitly stated otherwise. The optical data were measured at 20° C., unless explicitly stated otherwise.

In the present application and in the following examples the structures of the liquid crystal compounds are specified by acronyms, which can be transformed into chemical formulae according to the following Tables A and B. All the radicals $C_nH_{2n+1}$ and $C_mH_{2m+1}$ are straight-chain alkyl radicals having n or m C atoms n and m, independently of one another, denote 1, 2, 3, 4, 5, 6, 7, 8, 9, 10, 11, 12, 13, 14 or 15. The coding according to Table B is self-evident. Table A specifies the acronym for the parent body only. In individual cases, the acronym for the parent body is followed, separated therefrom by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| Nm | $C_nH_{2n+1}$ | $C_mH_{2m+1}$ | H | H |
| NOm | $C_nH_{2n+1}$ | $OC_mH_{2m+1}$ | H | H |
| NO.m | $OC_nH_{2n+1}$ | $C_mH_{2m+1}$ | H | H |
| N | $C_nH_{2n+1}$ | CN | H | H |
| nN.F | $C_nH_{2n+1}$ | CN | H | F |
| NF | $C_nH_{2n+1}$ | F | H | H |
| NOF | $OC_nH_{2n+1}$ | F | H | H |
| NCl | $C_nH_{2n+1}$ | Cl | H | H |
| nF.F | $C_nH_{2n+1}$ | F | H | F |
| nF.F.F | $C_nH_{2n+1}$ | F | F | F |
| NCF$_3$ | $C_nH_{2n+1}$ | $CF_3$ | H | H |
| nOCF$_3$ | $C_nH_{2n+1}$ | $OCF_3$ | H | H |
| nOCF$_2$ | $C_nH_{2n+1}$ | $OCHF_2$ | H | H |
| NS | $C_nH_{2n+1}$ | NCS | H | H |
| rVsN | $C_rH_{2r+1}-CH=CH-C_sH_{2s}-$ | CN | H | H |
| rEsN | $C_rH_{2r+1}-O-C_2H_{2s}-$ | CN | H | H |
| NAm | $C_nH_{2n+1}$ | $COOC_mH_{2m+1}$ | H | H |
| nOCCF$_2$.F.F | $C_nH_{2n+1}$ | $OCH_2CF_2H$ | F | F |

Preferred mixture components are listed in Tables A and B.

TABLE A

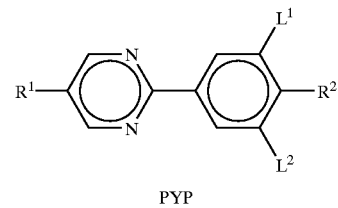

PYP

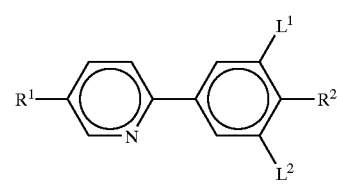

PYRP

TABLE A-continued
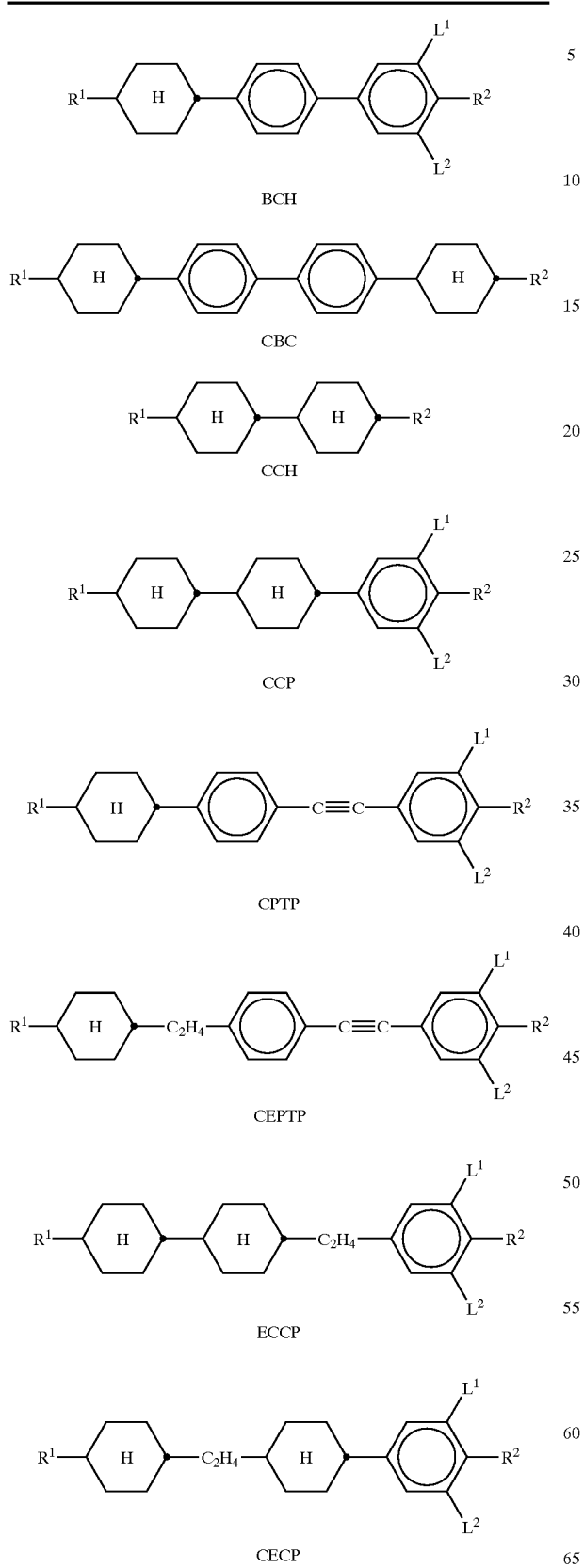
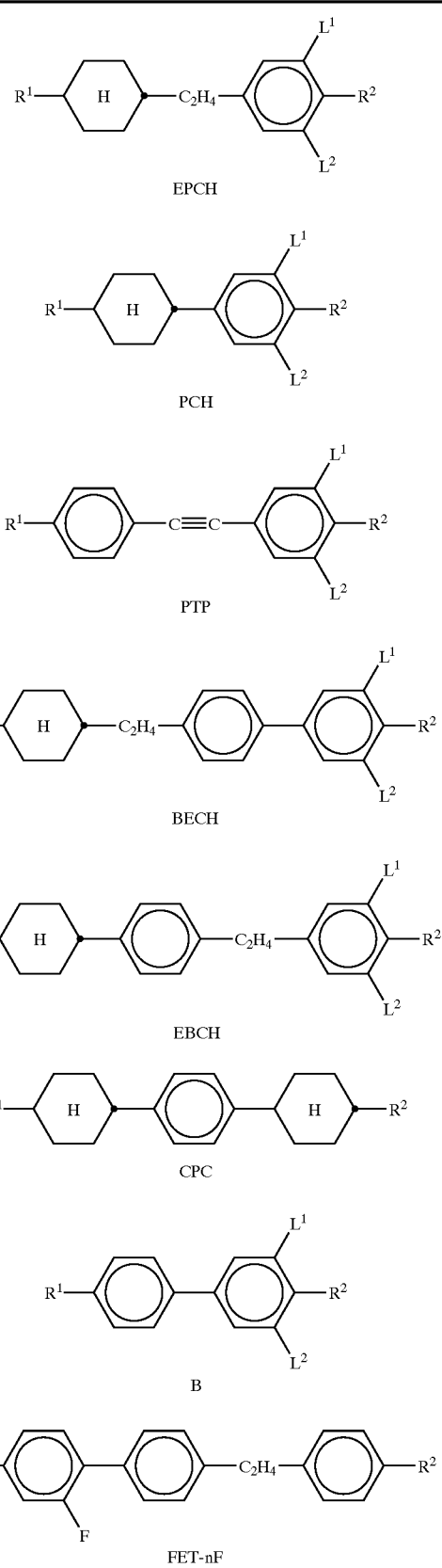

TABLE A-continued
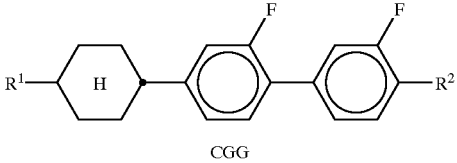
CGG
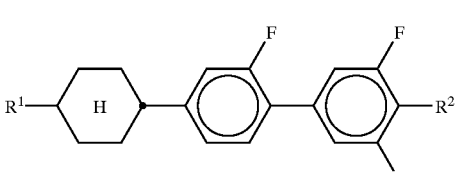
CGU
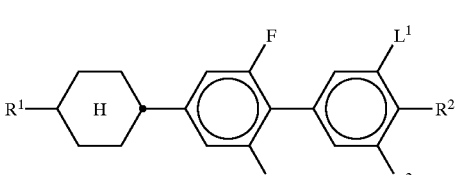
CUP
TABLE B
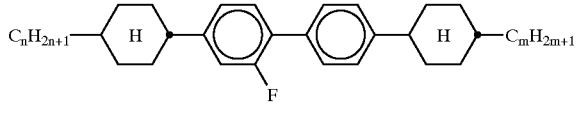
CBC-nmF
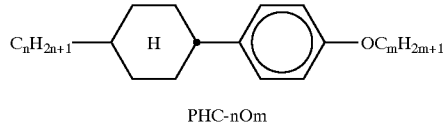
PHC-nOm
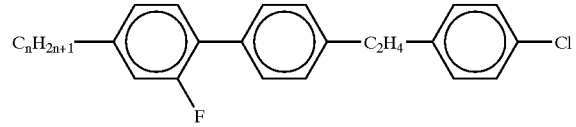
FET-nCl
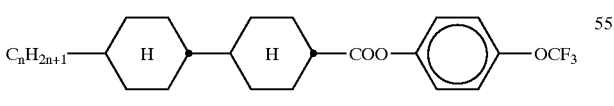
CP-nOCF$_3$
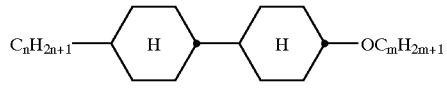
CCH-nOm
TABLE B-continued
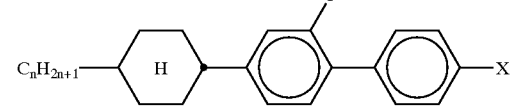
BCH-n.Fm
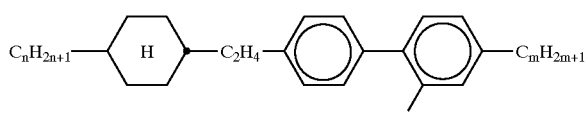
Inm
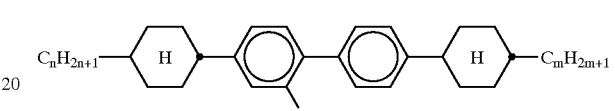
CBC-nmF
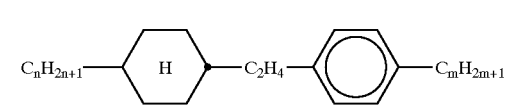
ECCP-nm
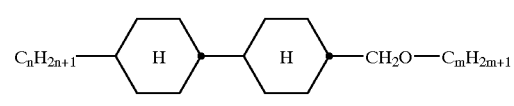
CCH-n1EM
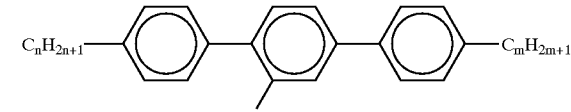
T-nFm
CGU-n-F
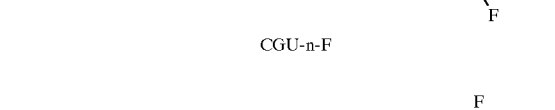
CCP-nOCF$_3$.F
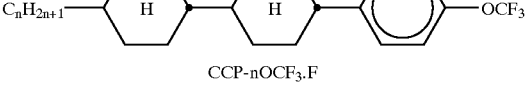
CGG-n-F TABLE B-continued
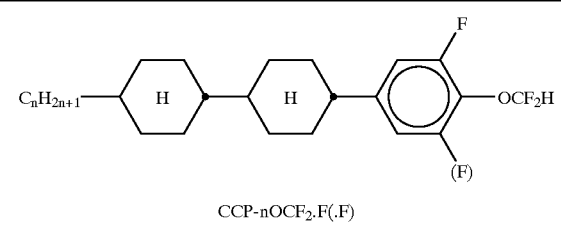
CCP-nOCF2.F(.F)
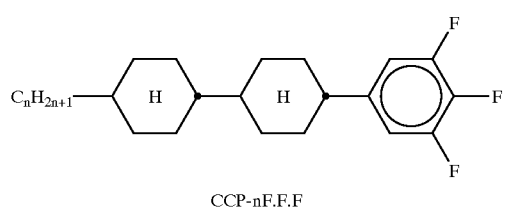
CCP-nF.F.F
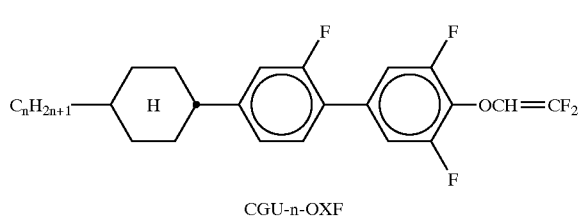
CGU-n-OXF
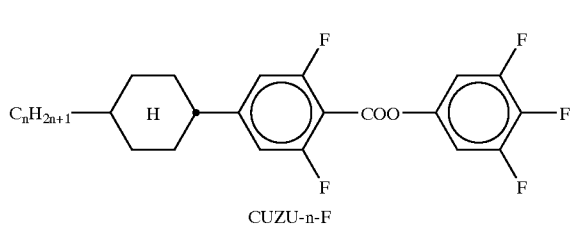
CUZU-n-F
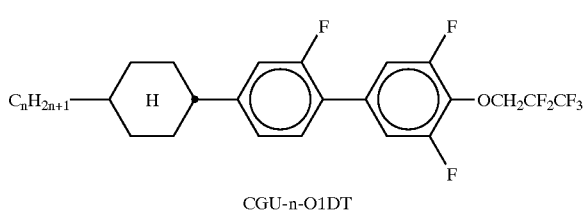
CGU-n-O1DT
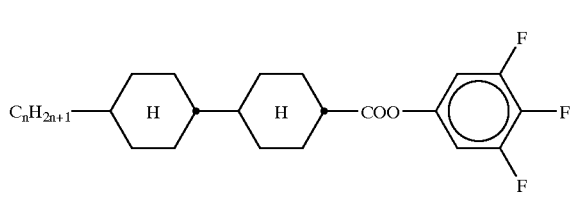
CCZU-n-F
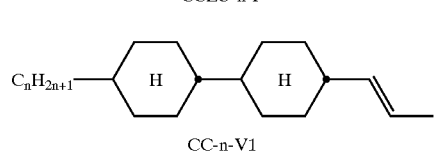
CC-n-V1
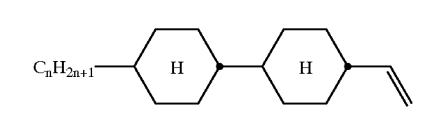
CC-n-V
TABLE B-continued
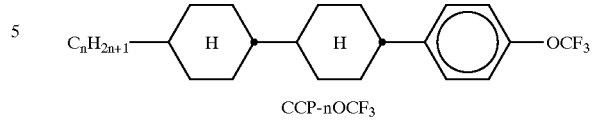
CCP-nOCF3
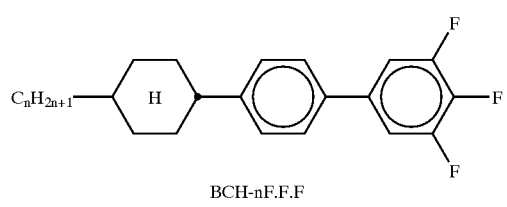
BCH-nF.F.F
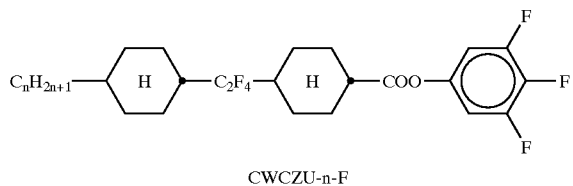
CWCZU-n-F
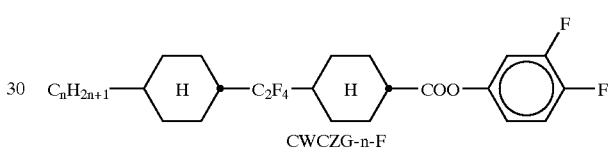
CWCZG-n-F
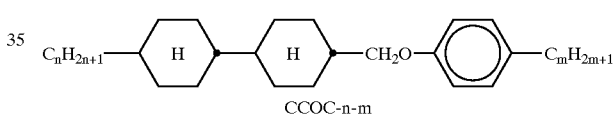
CCOC-n-m
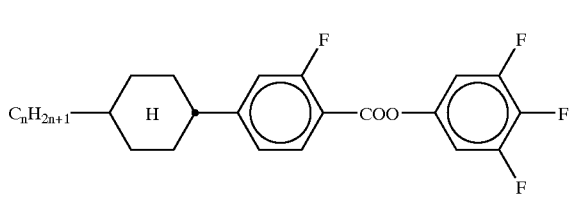
CGZU-n-F
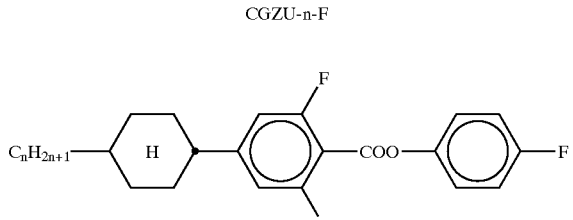
CUZP-n-F
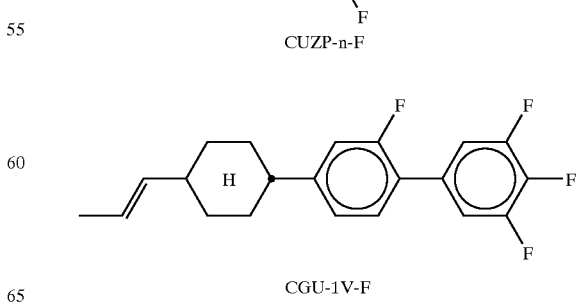
CGU-1V-F

TABLE B-continued
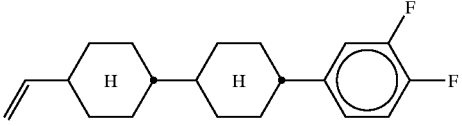
CCG-V-F
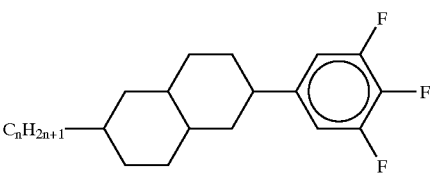
CGZP-n-F
UZP-n-N
CGZP-n-OT
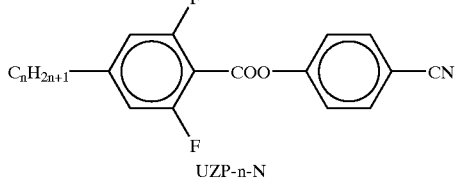
CUZP-n-OT
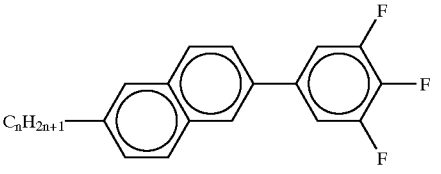
CCQU-n-F
TABLE B-continued
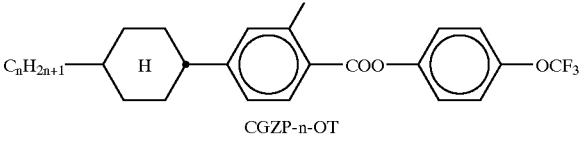
Dec-U-n-F
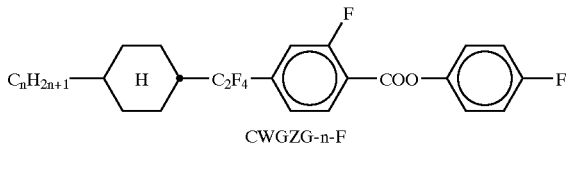
Nap-U-n-F
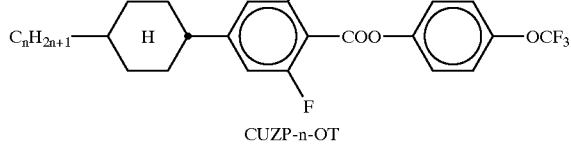
CWGZG-n-F
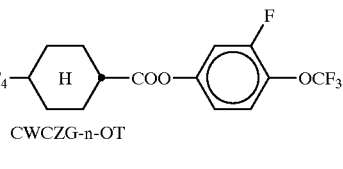
CWCZG-n-OT
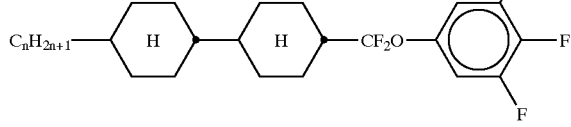
CWCZP-n-OT
Table C lists possible dopants which can be added to the mixtures according to the invention.
TABLE C
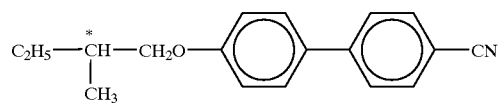
C 15
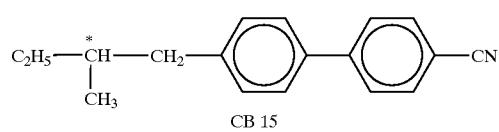
CB 15

TABLE C-continued
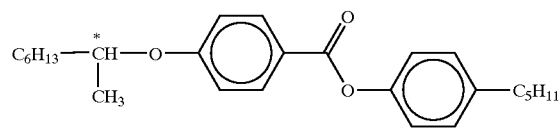
CM 21
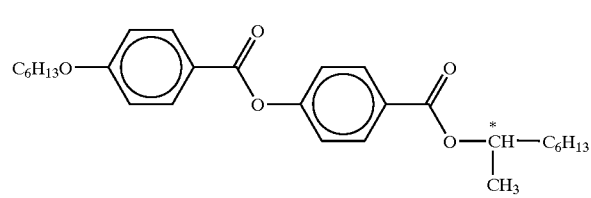
R/S 811
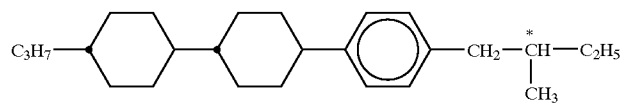
CM 44
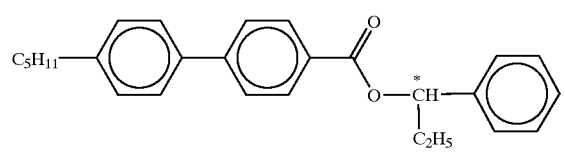
CM 45
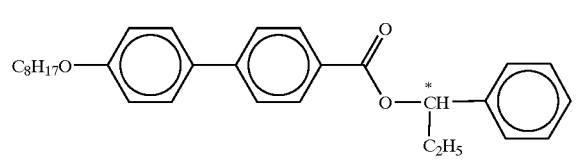
CM 47
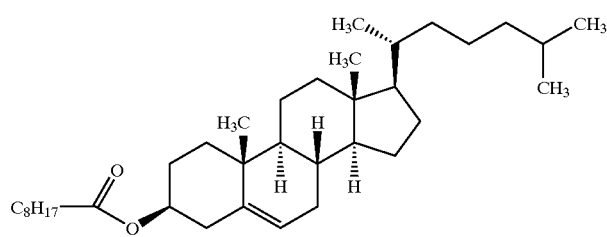
CN
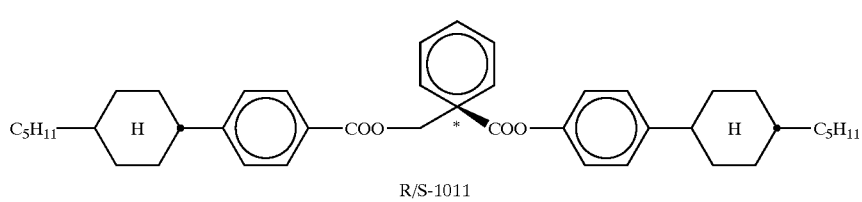
R/S-1011
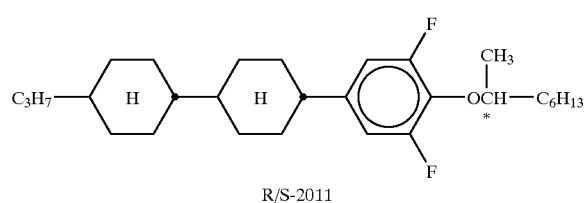
R/S-2011

TABLE C-continued
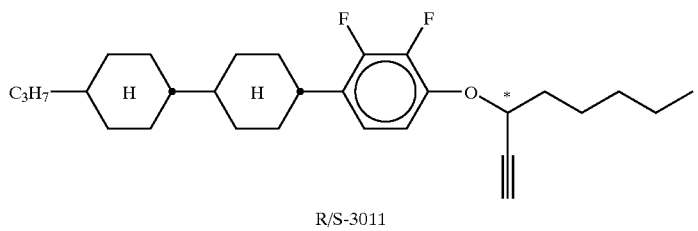
R/S-3011
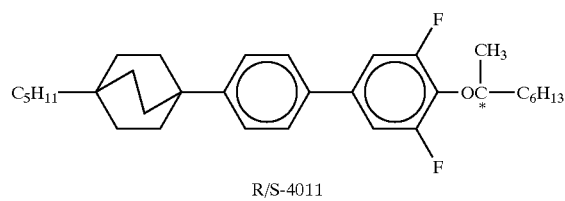
R/S-4011
Table D lists exemplary stabilizers which can be added to the mixtures according to the invention.
TABLE D
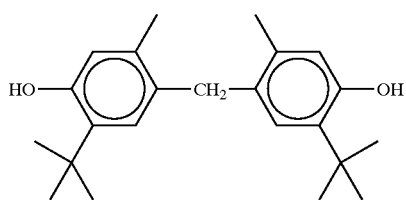
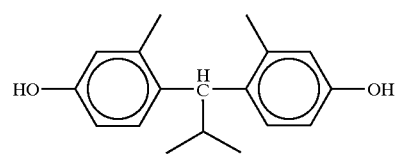
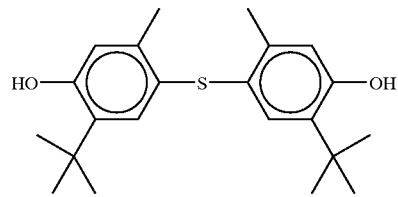
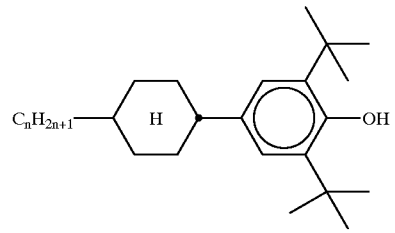
TABLE D-continued
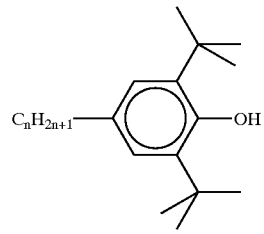
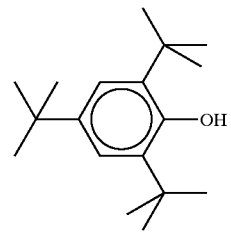
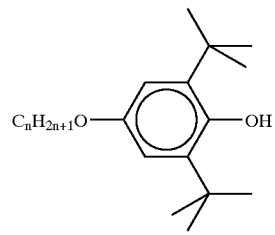
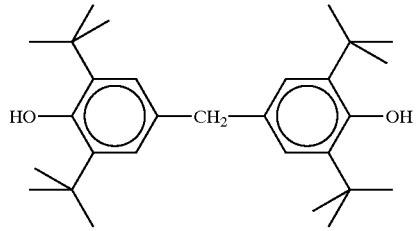

TABLE D-continued
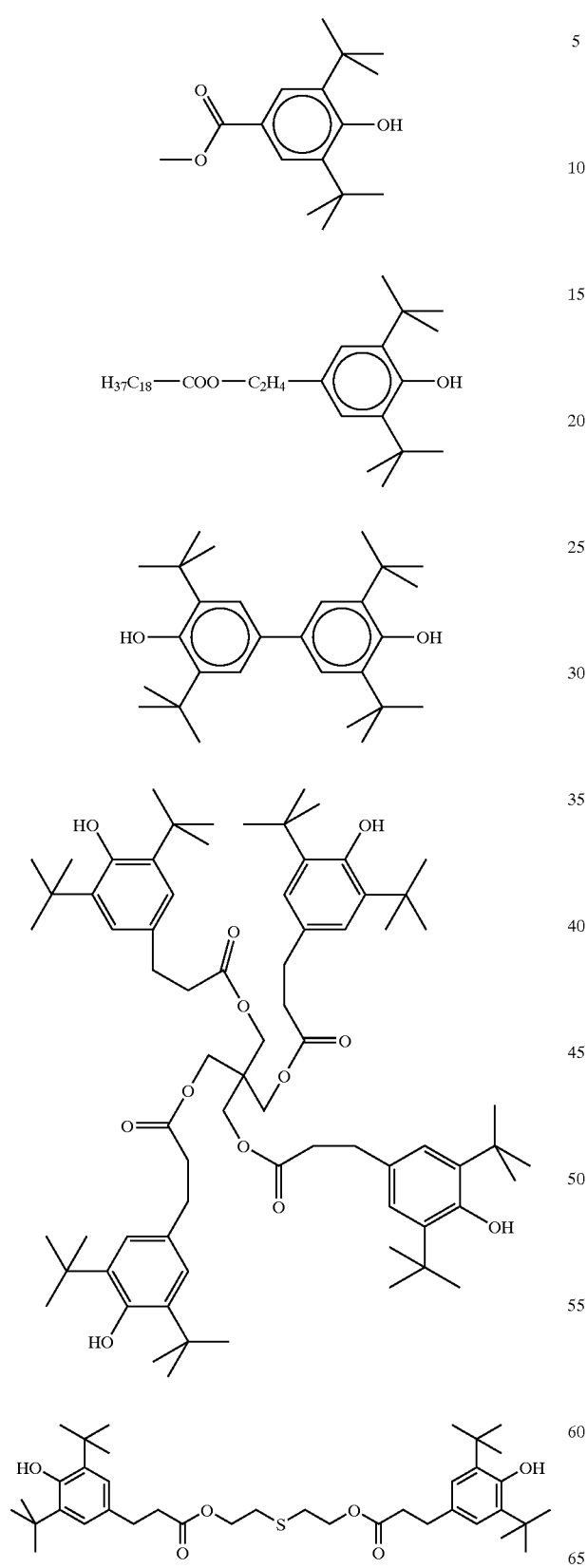
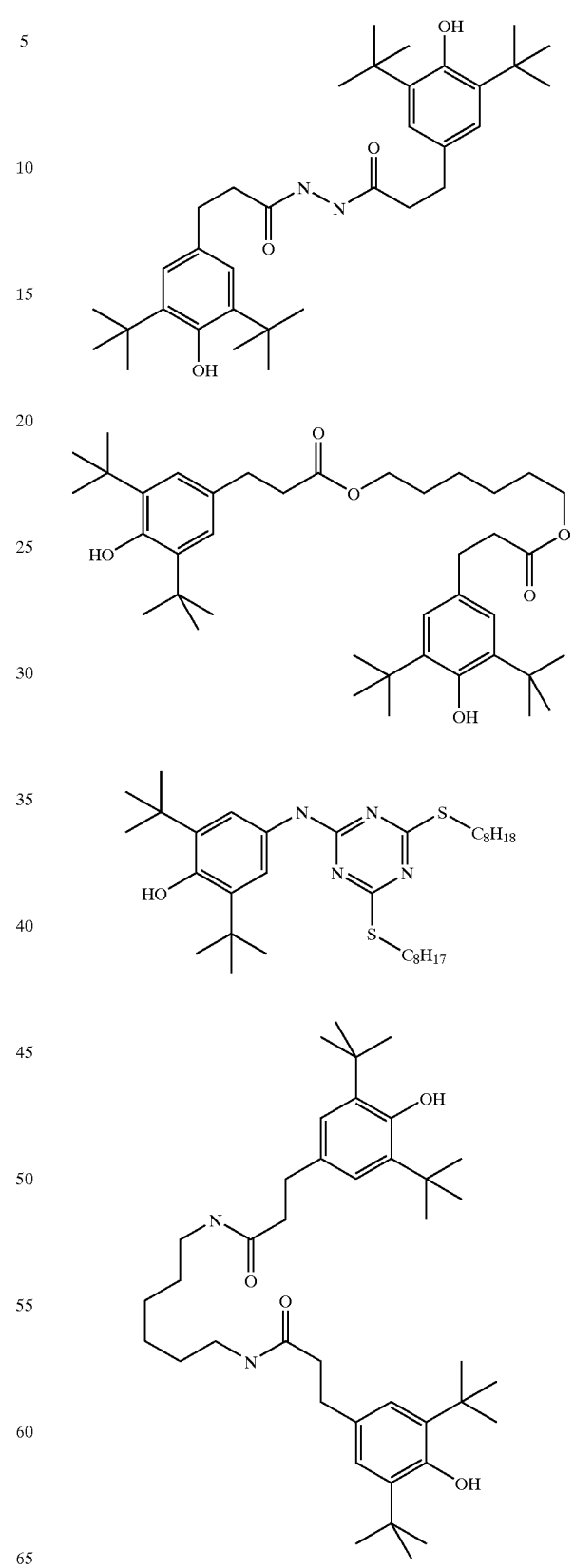

TABLE D-continued
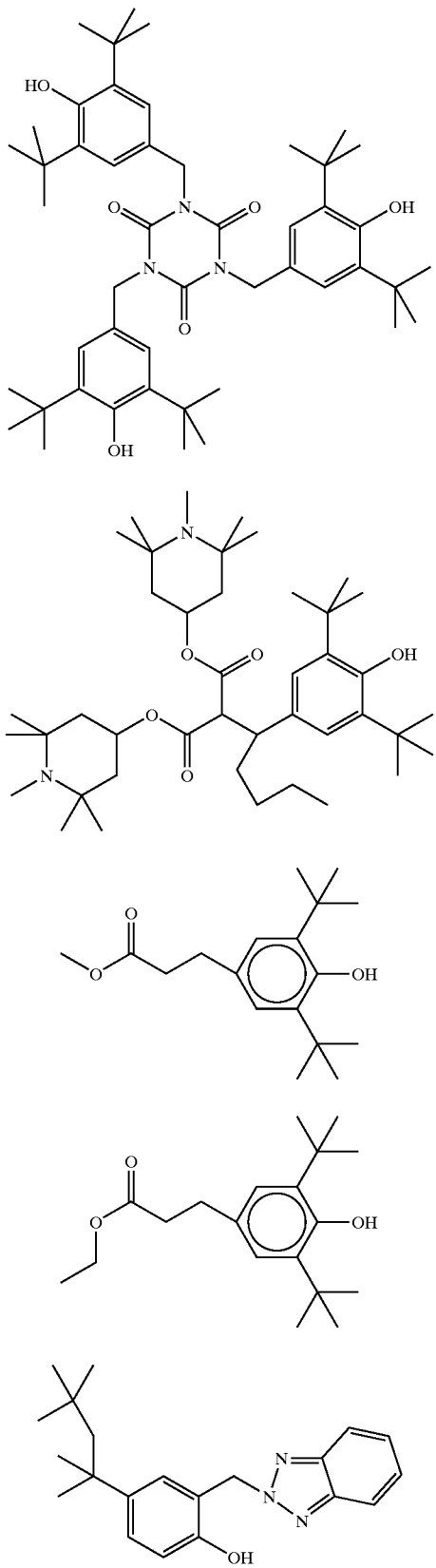
TABLE D-continued
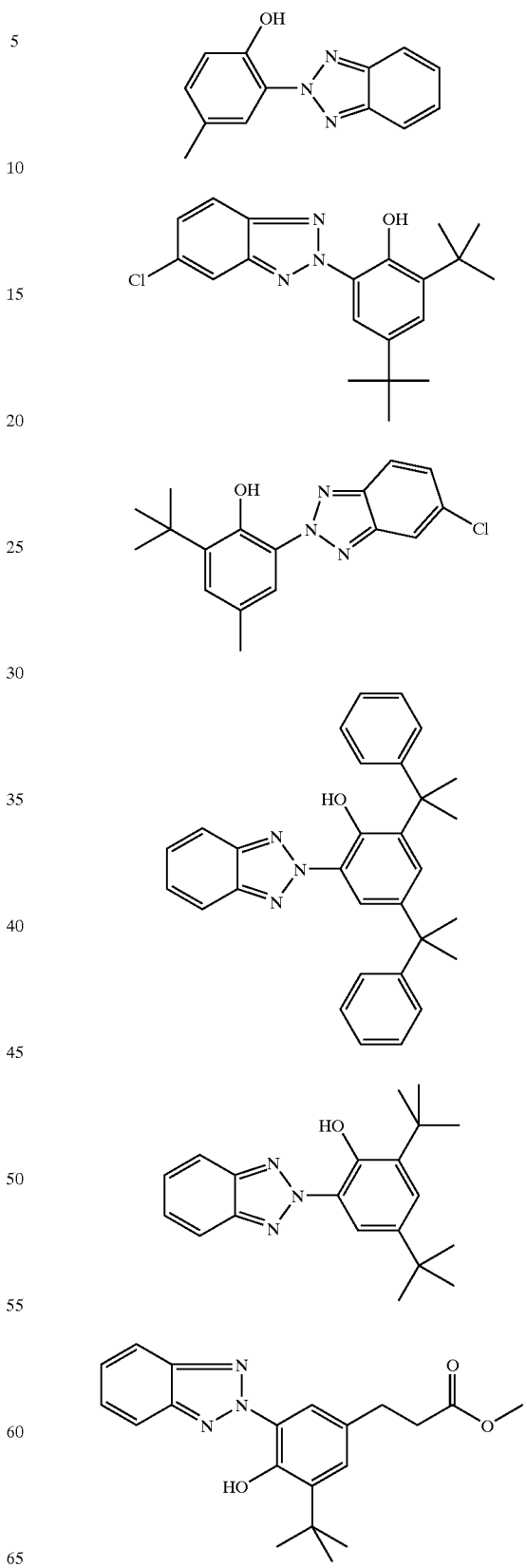

TABLE D-continued

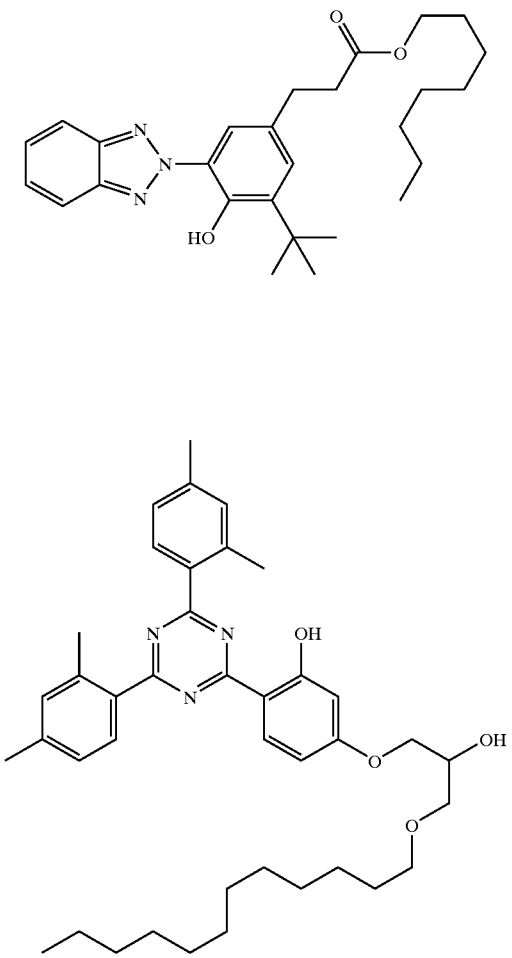

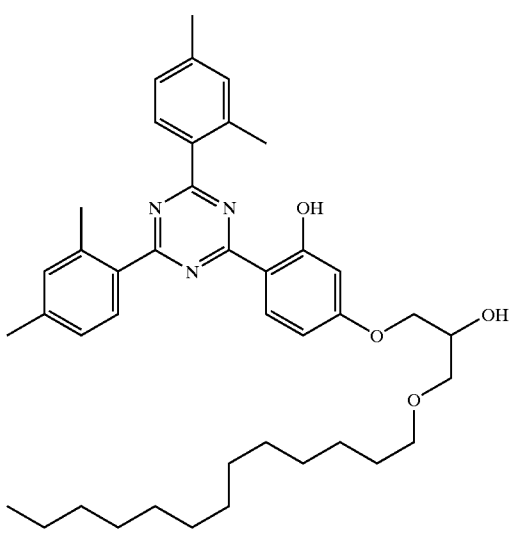

TABLE D-continued

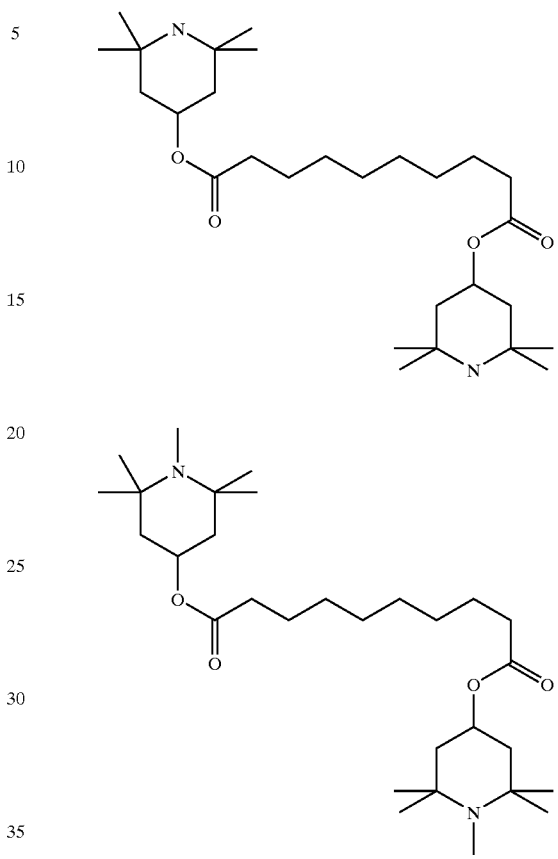

The following examples are intended to illustrate the invention without limiting it. Hereinbefore and hereinafter, percentages are given in per cent by weight. All temperatures are specified in degrees centigrade. M.p. means melting point, c.p. means clearing point, C means crystalline state, N means nematic phase, S means smectic phase, and I means isotropic phase. Data appearing between these symbols represent the transition temperatures. Δn means optical anisotropy (589 nm, 20° C.). The flow viscosity $v_{20}$ (mm$^2$/sec) and the rotational viscosity $\gamma_1$ [mPa·s] were each determined at 20° C.

"Standard work-up" means: water is added if required, the mixture is extracted with dichloromethane, diethyl ether, methyl tert-butyl ether or toluene, followed by phase separation, then drying of the organic phase, evaporation of the solvent and purification of the product by distillation under reduced pressure or crystallization and/or chromatography. The following abbreviations are used:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure of all applications, patents and publications, cited above or below, and of corresponding German application No. 10064996.3, filed Dec. 23, 2001 is hereby incorporated by reference.

EXAMPLE 1

Step 1.1

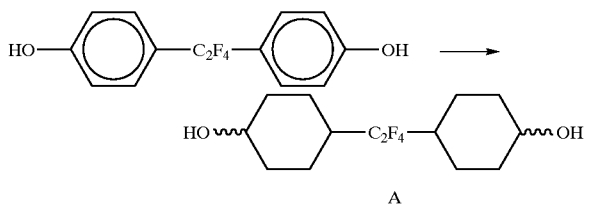

3.494 mol of 1,2-bis(4-hydroxyphenyl)tetrafluoroethane is dissolved in 15 l of isopropanol and hydrogenated with 400 g of 5% rhodium activated carbon at 60° C. and 5 bar. After the hydrogenation is complete, the catalyst is filtered off, the filtrate is concentrated and the residue is recrystallized from ethyl acetate.

Step 1.2

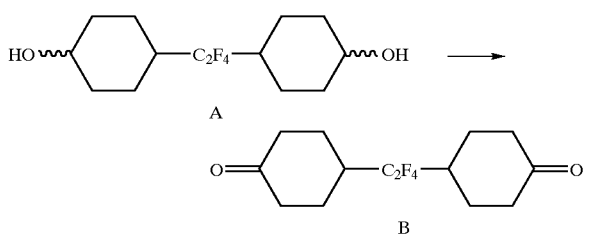

1.5 mol of pyridinium chlorochromate, 300 g of Celite® 545, (Celite® 545 is an additive used to prevent clogging during filtration, it comprises kieselguhr, i.e., diatomaceous earth), in 4 l of dichloromethane and 0.97 mol of A are stirred overnight at room temperature. The suspension is then filtered off with suction, washed with dichloromethane and is concentrated. The residue is stirred with 50 ml of petroleum ether/ethyl acetate (1:1), 1 g of activated carbon and 5 g of silica gel and is then filtered off with suction over silica gel. The filtrate is dissolved in dichloromethane and is stirred overnight with 25 g of pyridine: sulfur trioxide complex. Finally, the mixture is extracted with water and filtered off with suction over silica gel. M.p. is 125–126° C. (methylcyclohexane, i.e., product was recrystallized from methylcyclohexane before determination of the metling point).

Step 1.3

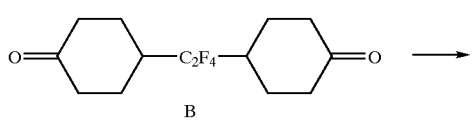

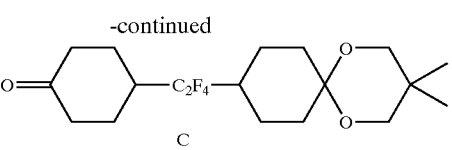

0.075 mol of B and 0.230 mol of 2,2-dimethyl-1,3-propane in 250 ml of cyclohexane are stirred at 60° C. for 24 h with 0.05 g of sulfuric acid and 250 ml of water. The mixture is allowed to cool to room temperature and the sediment is separated from the liquid phase by means of a sintered disc and is dried. The melting range is 146–158° C. (methylcyclohexane)

Step 1.4

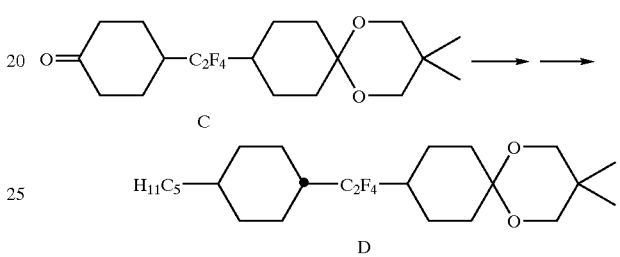

0.121 mol of C and 0.145 mol of pentyltriphenylphosphonium bromide in 400 ml of anhydrous THF are cooled to −10° C. and admixed, with stirring, with 0.160 mol of potassium t-butylate in 100 ml of anhydrous THF. The reaction solution is stirred overnight at room temperature. This is followed by standard work-up. The crude product together with n-hexane is filtered off with suction over silica gel. The filtrate is concentrated and the residue is dissolved in 600 ml of THF. 8 g of Pd—C (5%) are added, followed by hydrogenation at 1 bar at room temperature.

Step 1.5

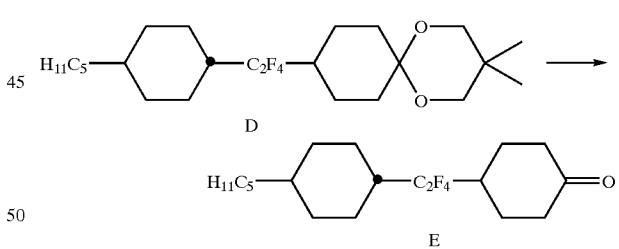

0.041 mol of D 300 ml of toluene and 100 ml of formic acid are stirred for 2 days at room temperature. The formic acid phase is diluted with water, extracted with toluene, and the combined toluene phases are finally subjected of standard work-up. The melting range is 64–86.1° C. (methylcyclohexane)

Step 1.6

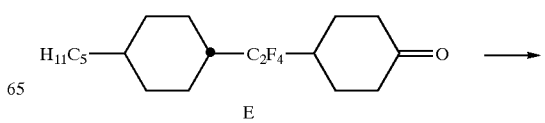

-continued

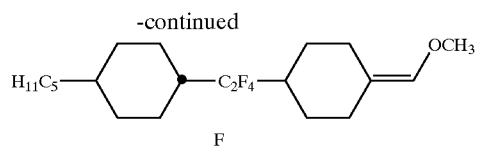

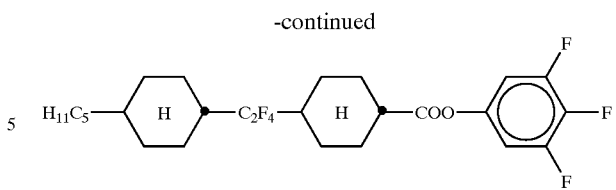

0.105 mol of E, and 0.119 mol of methoxymethyltriphenylphosphonium chloride are produced as an initial charge in 450 ml of THF, and a solution of 0.134 mol of potassium t-butylate in 150 ml of THF is added dropwise with ice cooling. The reaction mixture is stirred overnight at room temperature, and the mixture is finally subjected to standard work-up.

Step 1.7

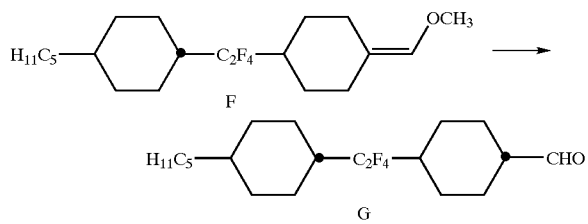

0.061 mol of F, and 2.915 mol of formic acid in 200 ml of toluene are stirred overnight at room temperature. The mixture is then subjected to standard work-up.

To carry out the isomerization, 0.083 mol of the product, 600 ml of methanol and 0.135 mol of sodium hydroxide solution are stirred for 2 h at room temperature, followed by stirring for a further 2 h at −20° C. The precipitated product is filtered off with suction and washed with methanol.

Step 1.8

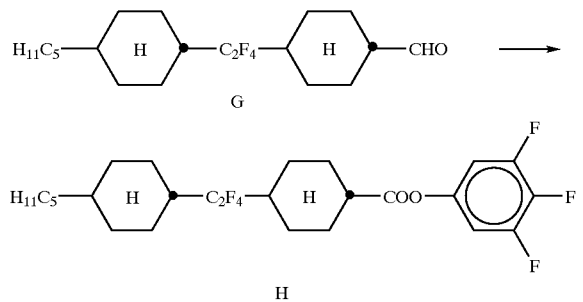

0.042 mol of G in 300 ml of acetone are admixed at room temperature with 0.107 mol of chromic acid. The mixture is stirred at room temperature for 24 h. The excess of $CrO_3$ is removed with isopropanol. The reaction mixture is subjected to standard work-up. The crude product is recrystallized from acetone at 0° C. C ? $S_x$ 253 N 258 I.

Step 1.9

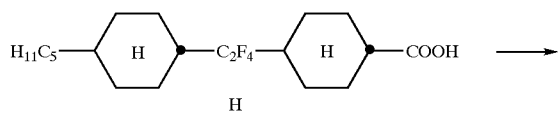

0.009 mol of H, 0.009 mol of 3,4,5-trifluorophenol and 0.010 mol of 4-(dimethylamino)pyridine are introduced as an initial charge in 30 ml of toluene. Added dropwise to this mixture at 10° C. is 0.010 mol of N,N-dicyclohexylcarbodiimide in 10 ml of toluene. The reaction mixture is stirred at room temperature for 48 h and is then admixed with 1.586 mmol of oxalic acid dihydrate and stirred for a further hour.

The product is filtered off with suction over silica gel and the filtrate is concentrated. The crude product is purified via a silica gel column (petroleum ether/MTB ether 9:1). The product is recrystallized from n-heptane. C 47 $S_B$ 109 N 173.2 I; $\Delta\epsilon=8.8$; $\Delta n=0.724$, $\gamma_1=342$ The following compounds of the formula

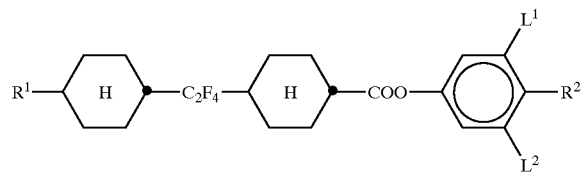

are prepared in a similar manner:

| $R^1$ | $R^2$ | $L^1$ | $L^2$ |
|---|---|---|---|
| $CH_3$ | F | H | H |
| $CH_3$ | F | F | H |
| $CH_3$ | F | F | F |
| $C_2H_5$ | F | H | H |
| $C_2H_5$ | F | F | H |
| $C_2H_5$ | F | F | F |
| $n-C_3H_7$ | F | H | H |
| $n-C_3H_7$ | F | F | H |
| $n-C_3H_7$ | F | F | F |
| $n-C_4H_9$ | F | H | H |
| $n-C_4H_9$ | F | F | H |
| $n-C_4H_9$ | F | F | F |
| $n-C_5H_{11}$ | F | H | H |
| $n-C_5H_{11}$ | F | F | H |
| $n-C_6H_{13}$ | F | H | H |
| $n-C_6H_{13}$ | F | F | H |
| $n-C_6H_{13}$ | F | F | F |
| $n-C_7H_{13}$ | F | H | H |
| $n-C_7H_{13}$ | F | F | H |
| $n-C_7H_{13}$ | F | F | F |
| $CH_2=CH$ | F | H | H |
| $CH_2=CH$ | F | F | H |
| $CH_2=CH$ | F | F | F |
| $CH_3CH=CH$ | F | H | H |
| $CH_3CH=CH$ | F | F | H |
| $CH_3CH=CH$ | F | F | F |
| $CH_2=CHC_2H_4$ | F | H | H |
| $CH_2=CHC_2H_4$ | F | F | H |
| $CH_2=CHC_2H_4$ | F | F | F |
| $CH_3CH=CHC_2H_4$ | F | H | H |
| $CH_3CH=CHC_2H_4$ | F | F | H |
| $CH_3CH=CHC_2H_4$ | F | F | F |
| $(CH_3)_2CH$ | F | H | H |
| $(CH_3)_2CH$ | F | F | H |

| R¹ | R² | L¹ | L² |
|---|---|---|---|
| (CH₃)₂CH | F | F | F |
| (CH₃)₂CHCH₂ | F | H | H |
| (CH₃)₂CHCH₂ | F | F | H |
| (CH₃)₂CHCH₂ | F | F | F |
| CH₃ | OCF₃ | H | H |
| CH₃ | OCF₃ | F | H |
| CH₃ | OCF₃ | F | F |
| C₂H₅ | OCF₃ | H | H |
| C₂H₅ | OCF₃ | F | H |
| C₂H₅ | OCF₃ | F | F |
| n-C₃H₇ | OCF₃ | H | H |
| n-C₃H₇ | OCF₃ | F | H |
| n-C₃H₇ | OCF₃ | F | F |
| n-C₄H₉ | OCF₃ | H | H |
| n-C₄H₉ | OCF₃ | F | H |
| n-C₄H₉ | OCF₃ | F | F |
| n-C₅H₁₁ | OCF₃ | H | H |
| n-C₅H₁₁ | OCF₃ | F | H |
| n-C₅H₁₁ | OCF₃ | F | F |
| n-C₆H₁₃ | OCF₃ | H | H |
| n-C₆H₁₃ | OCF₃ | F | H |
| n-C₆H₁₃ | OCF₃ | F | F |
| n-C₇H₁₅ | OCF₃ | H | H |
| n-C₇H₁₅ | OCF₃ | F | H |
| n-C₇H₁₅ | OCF₃ | F | F |
| CH₂=CH | OCF₃ | H | H |
| CH₂=CH | OCF₃ | F | H |
| CH₂=CH | OCF₃ | F | F |
| CH₃CH=CH | OCF₃ | H | H |
| CH₃CH=CH | OCF₃ | F | H |
| CH₃CH=CH | OCF₃ | F | F |
| CH₂=CHC₂H₄ | OCF₃ | H | H |
| CH₂=CHC₂H₄ | OCF₃ | F | H |
| CH₂=CHC₂H₄ | OCF₃ | F | F |
| CH₃CH=CHC₂H₄ | OCF₃ | H | H |
| CH₃CH=CHC₂H₄ | OCF₃ | F | H |
| CH₃CH=CHC₂H₄ | OCF₃ | F | F |
| (CH₃)₂CH | OCF₃ | H | H |
| (CH₃)₂CH | OCF₃ | F | H |
| (CH₃)₂CH | OCF₃ | F | F |
| (CH₃)₂CHCH₂ | OCF₃ | H | H |
| (CH₃)₂CHCH₂ | OCF₃ | F | H |
| (CH₃)₂CHCH₂ | OCF₃ | F | F |
| CH₃ | OCHFCF₃ | H | H |
| CH₃ | OCHFCF₃ | F | H |
| CH₃ | OCHFCF₃ | F | F |
| C₂H₅ | OCHFCF₃ | H | H |
| C₂H₅ | OCHFCF₃ | F | H |
| C₂H₅ | OCHFCF₃ | F | F |
| n-C₃H₇ | OCHFCF₃ | H | H |
| n-C₃H₇ | OCHFCF₃ | F | H |
| n-C₃H₇ | OCHFCF₃ | F | F |
| n-C₄H₉ | OCHFCF₃ | H | H |
| n-C₄H₉ | OCHFCF₃ | F | H |
| n-C₄H₉ | OCHFCF₃ | F | F |
| n-C₅H₁₁ | OCHFCF₃ | H | H |
| n-C₅H₁₁ | OCHFCF₃ | F | H |
| n-C₅H₁₁ | OCHFCF₃ | F | F |
| n-C₆H₁₃ | OCHFCF₃ | H | H |
| n-C₆H₁₃ | OCHFCF₃ | F | H |
| n-C₆H₁₃ | OCHFCF₃ | F | F |
| CH₂=CH | OCHFCF₃ | H | H |
| CH₂=CH | OCHFCF₃ | F | H |
| CH₂=CH | OCHFCF₃ | F | F |
| CH₃CH=CH | OCHFCF₃ | H | H |
| CH₃CH=CH | OCHFCF₃ | F | H |
| CH₃CH=CH | OCHFCF₃ | F | F |
| CH₂=CHC₂H₄ | OCHFCF₃ | H | H |
| CH₂=CHC₂H₄ | OCHFCF₃ | F | H |
| CH₂=CHC₂H₄ | OCHFCF₃ | F | F |
| CH₃CH=CHC₂H₄ | OCHFCF₃ | H | H |
| CH₃CH=CHC₂H₄ | OCHFCF₃ | F | H |
| CH₃CH=CHC₂H₄ | OCHFCF₃ | F | F |
| (CH₃)₂CH | OCHFCF₃ | H | H |
| (CH₃)₂CH | OCHFCF₃ | F | H |
| (CH₃)₂CH | OCHFCF₃ | F | F |
| (CH₃)₂CHCH₂ | OCHFCF₃ | H | H |
| (CH₃)₂CHCH₂ | OCHFCF₃ | F | H |
| (CH₃)₂CHCH₂ | OCHFCF₃ | F | F |
| CH₃ | OCF₂CHFCF₃ | H | H |
| CH₃ | OCF₂CHFCF₃ | F | H |
| CH₃ | OCF₂CHFCF₃ | F | F |
| C₂H₅ | OCF₂CHFCF₃ | H | H |
| C₂H₅ | OCF₂CHFCF₃ | F | H |
| C₂H₅ | OCF₂CHFCF₃ | F | F |
| n-C₃H₇ | OCF₂CHFCF₃ | H | H |
| n-C₃H₇ | OCF₂CHFCF₃ | F | H |
| n-C₃H₇ | OCF₂CHFCF₃ | F | F |
| n-C₄H₉ | OCF₂CHFCF₃ | H | H |
| n-C₄H₉ | OCF₂CHFCF₃ | F | H |
| n-C₄H₉ | OCF₂CHFCF₃ | F | F |
| n-C₅H₁₁ | OCF₂CHFCF₃ | H | H |
| n-C₅H₁₁ | OCF₂CHFCF₃ | F | H |
| n-C₅H₁₁ | OCF₂CHFCF₃ | F | F |
| n-C₆H₁₃ | OCF₂CHFCF₃ | H | H |
| n-C₆H₁₃ | OCF₂CHFCF₃ | F | H |
| n-C₆H₁₃ | OCF₂CHFCF₃ | F | F |
| CH₂=CH | OCF₂CHFCF₃ | H | H |
| CH₂=CH | OCF₂CHFCF₃ | F | H |
| CH₂=CH | OCF₂CHFCF₃ | F | F |
| CH₃CH=CH | OCF₂CHFCF₃ | H | H |
| CH₃CH=CH | OCF₂CHFCF₃ | F | H |
| CH₃CH=CH | OCF₂CHFCF₃ | F | F |
| CH₂=CHC₂H₄ | OCF₂CHFCF₃ | H | H |
| CH₂=CHC₂H₄ | OCF₂CHFCF₃ | F | H |
| CH₂=CHC₂H₄ | OCF₂CHFCF₃ | F | F |
| CH₃CH=CHC₂H₄ | OCF₂CHFCF₃ | H | H |
| CH₃CH=CHC₂H₄ | OCF₂CHFCF₃ | F | H |
| CH₃CH=CHC₂H₄ | OCF₂CHFCF₃ | F | F |
| (CH₃)₂CH | OCF₂CHFCF₃ | H | H |
| (CH₃)₂CH | OCF₂CHFCF₃ | F | H |
| (CH₃)₂CH | OCF₂CHFCF₃ | F | F |
| (CH₃)₂CHCH₂ | OCF₂CHFCF₃ | H | H |
| (CH₃)₂CHCH₂ | OCF₂CHFCF₃ | F | H |
| (CH₃)₂CHCH₂ | OCF₂CHFCF₃ | F | F |
| CH₃ | OCHF₂ | H | H |
| CH₃ | OCHF₂ | F | H |
| CH₃ | OCHF₂ | F | F |
| C₂H₅ | OCHF₂ | H | H |
| C₂H₅ | OCHF₂ | F | H |
| C₂H₅ | OCHF₂ | F | F |
| n-C₃H₇ | OCHF₂ | H | H |
| n-C₃H₇ | OCHF₂ | F | H |
| n-C₃H₇ | OCHF₂ | F | F |
| n-C₄H₉ | OCHF₂ | H | H |
| n-C₄H₉ | OCHF₂ | F | H |
| n-C₄H₉ | OCHF₂ | F | F |
| n-C₅H₁₁ | OCHF₂ | H | H |
| n-C₅H₁₁ | OCHF₂ | F | H |
| n-C₅H₁₁ | OCHF₂ | F | F |
| n-C₆H₁₃ | OCHF₂ | H | H |
| n-C₆H₁₃ | OCHF₂ | F | H |
| n-C₆H₁₃ | OCHF₂ | F | F |
| CH₂=CH | OCHF₂ | H | H |
| CH₂=CH | OCHF₂ | F | H |
| CH₂=CH | OCHF₂ | F | F |
| CH₃CH=CH | OCHF₂ | H | H |
| CH₃CH=CH | OCHF₂ | F | H |
| CH₃CH=CH | OCHF₂ | F | F |
| CH₂=CHC₂H₄ | OCHF₂ | H | H |
| CH₂=CHC₂H₄ | OCHF₂ | F | H |
| CH₂=CHC₂H₄ | OCHF₂ | F | F |
| CH₃CH=CHC₂H₄ | OCHF₂ | H | H |
| CH₃CH=CHC₂H₄ | OCHF₂ | F | H |
| CH₃CH=CHC₂H₄ | OCHF₂ | F | F |
| (CH₃)₂CH | OCHF₂ | H | H |
| (CH₃)₂CH | OCHF₂ | F | H |
| (CH₃)₂CH | OCHF₂ | F | F |
| (CH₃)₂CHCH₂ | OCHF₂ | H | H |
| (CH₃)₂CHCH₂ | OCHF₂ | F | H |
| (CH₃)₂CHCH₂ | OCHF₂ | F | F |
| CH₃ | CF₃ | H | H |
| CH₃ | CF₃ | F | H |
| CH₃ | CF₃ | F | F |

| R¹ | R² | L¹ | L² |
|---|---|---|---|
| C₂H₅ | CF₃ | H | H |
| C₂H₅ | CF₃ | F | H |
| C₂H₅ | CF₃ | F | F |
| n-C₃H₇ | CF₃ | H | H |
| n-C₃H₇ | CF₃ | F | H |
| n-C₃H₇ | CF₃ | F | F |
| n-C₄H₉ | CF₃ | H | H |
| n-C₄H₉ | CF₃ | F | H |
| n-C₄H₉ | CF₃ | F | F |
| n-C₅H₁₁ | CF₃ | H | H |
| n-C₅H₁₁ | CF₃ | F | H |
| n-C₅H₁₁ | CF₃ | F | F |
| n-C₆H₁₃ | CF₃ | H | H |
| n-C₆H₁₃ | CF₃ | F | H |
| n-C₆H₁₃ | CF₃ | F | F |
| CH₂=CH | CF₃ | H | H |
| CH₂=CH | CF₃ | F | H |
| CH₂=CH | CF₃ | F | F |
| CH₃CH=CH | CF₃ | H | H |
| CH₃CH=CH | CF₃ | F | H |
| CH₃CH=CH | CF₃ | F | F |
| CH₂=CHC₂H₄ | CF₃ | H | H |
| CH₂=CHC₂H₄ | CF₃ | F | H |
| CH₂=CHC₂H₄ | CF₃ | F | F |
| CH₃CH=CHC₂H₄ | CF₃ | H | H |
| CH₃CH=CHC₂H₄ | CF₃ | F | H |
| CH₃CH=CHC₂H₄ | CF₃ | F | F |
| (CH₃)₂CH | CF₃ | H | H |
| (CH₃)₂CH | CF₃ | F | H |
| (CH₃)₂CH | CF₃ | F | F |
| (CH₃)₂CHCH₂ | CF₃ | H | H |
| (CH₃)₂CHCH₂ | CF₃ | F | H |
| (CH₃)₂CHCH₂ | CF₃ | F | F |
| CH₃ | CN | H | H |
| CH₃ | CN | F | H |
| CH₃ | CN | F | F |
| C₂H₅ | CN | H | H |
| C₂H₅ | CN | F | H |
| C₂H₅ | CN | F | F |
| n-C₃H₇ | CN | H | H |
| n-C₃H₇ | CN | F | H |
| n-C₃H₇ | CN | F | F |
| n-C₄H₉ | CN | H | H |
| n-C₄H₉ | CN | F | H |
| n-C₄H₉ | CN | F | F |
| n-C₅H₁₁ | CN | H | H |
| n-C₅H₁₁ | CN | F | H |
| n-C₅H₁₁ | CN | F | F |
| n-C₆H₁₃ | CN | H | H |
| n-C₆H₁₃ | CN | F | H |
| n-C₆H₁₃ | CN | F | F |
| CH₂=CH | CN | H | H |
| CH₂=CH | CN | F | H |
| CH₂=CH | CN | F | F |
| CH₃CH=CH | CN | H | H |
| CH₃CH=CH | CN | F | H |
| CH₃CH=CH | CN | F | F |
| CH₂=CHC₂H₄ | CN | H | H |
| CH₂=CHC₂H₄ | CN | F | H |
| CH₂=CHC₂H₄ | CN | F | F |
| CH₃CH=CHC₂H₄ | CN | H | H |
| CH₃CH=CHC₂H₄ | CN | F | H |
| CH₃CH=CHC₂H₄ | CN | F | F |
| (CH₃)₂CH | CN | H | H |
| (CH₃)₂CH | CN | F | H |
| (CH₃)₂CH | CN | F | F |
| (CH₃)₂CHCH₂ | CN | H | H |
| (CH₃)₂CHCH₂ | CN | F | H |
| (CH₃)₂CHCH₂ | CN | F | F |
| CH₃ | SF₅ | H | H |
| CH₃ | SF₅ | F | H |
| CH₃ | SF₅ | F | F |
| C₂H₅ | SF₅ | H | H |
| C₂H₅ | SF₅ | F | H |
| C₂H₅ | SF₅ | F | F |
| n-C₃H₇ | SF₅ | H | H |
| n-C₃H₇ | SF₅ | F | H |
| n-C₃H₇ | SF₅ | F | F |
| n-C₄H₉ | SF₅ | H | H |
| n-C₄H₉ | SF₅ | F | H |
| n-C₄H₉ | SF₅ | F | F |
| n-C₅H₁₁ | SF₅ | H | H |
| n-C₅H₁₁ | SF₅ | F | H |
| n-C₅H₁₁ | SF₅ | F | F |
| n-C₆H₁₃ | SF₅ | H | H |
| n-C₆H₁₃ | SF₅ | F | H |
| n-C₆H₁₃ | 5F₅ | F | F |
| CH₂=CH | SF₅ | H | H |
| CH₂=CH | 5F₅ | F | H |
| CH₂=CH | SF₅ | F | F |
| CH₃CH=CH | SF₅ | H | H |
| CH₃CH=CH | SF₅ | F | H |
| CH₃CH=CH | SF₅ | F | F |
| CH₂=CHC₂H₄ | 5F₅ | H | H |
| CH₂=CHC₂H₄ | SF₅ | F | H |
| CH₂=CHC₂H₄ | SF₅ | F | F |
| CH₃CH=CHC₂H₄ | SF₅ | H | H |
| CH₃CH=CHC₂H₄ | 5F₅ | F | H |
| CH₃CH=CHC₂H₄ | SF₅ | F | F |
| (CH₃)₂CH | SF₅ | H | H |
| (CH₃)₂CH | SF₅ | F | H |
| (CH₃)₂CH | SF₅ | F | F |
| (CH₃)₂CHCH₂ | SF₅ | H | H |
| (CH₃)₂CHCH₂ | SF₅ | F | H |
| (CH₃)₂CHCH₂ | 5F₅ | F | F |
| CH₃ | OCH=CF₂ | H | H |
| CH₃ | OCH=CF₂ | F | H |
| CH₃ | OCH=CF₂ | F | F |
| C₂H₅ | OCH=CF₂ | H | H |
| C₂H₅ | OCH=CF₂ | F | H |
| C₂H₅ | QCH=CF₂ | F | F |
| n-C₃H₇ | OCH=CF₂ | H | H |
| n-C₃H₇ | OCH=CF₂ | F | H |
| n-C₃H₇ | OCH=CF₂ | F | F |
| n-C₄H₉ | OCH=CF₂ | H | H |
| n-C₄H₉ | OCH=CF₂ | F | H |
| n-C₄H₉ | OCH=CF₂ | F | F |
| n-C₅H₁₁ | OCH=CF₂ | H | H |
| n-C₅H₁₁ | OCH=CF₂ | F | H |
| n-C₅H₁₁ | OCH=CF₂ | F | F |
| n-C₆H₁₃ | OCH=CF₂ | H | H |
| n-C₆H₁₃ | OCH=CF₂ | F | H |
| n-C₆H₁₃ | OCH=CF₂ | F | F |
| CH₂=CH | OCH=CF₂ | H | H |
| CH₂=CH | OCH=CF₂ | F | H |
| CH₂=CH | OCH=CF₂ | F | F |
| CH₃CH=CH | OCH=CF₂ | H | H |
| CH₃CH=CH | OCH=CF₂ | F | H |
| CH₃CH=CH | OCH=CF₂ | F | F |
| CH₂=CHC₂H₄ | OCH=CF₂ | H | H |
| CH₂=CHC₂H₄ | OCH=CF₂ | F | H |
| CH₂=CHC₂H₄ | OCH=CF₂ | F | F |
| CH₃CH=CHC₂H₄ | OCH=CF₂ | H | H |
| CH₃CH=CHC₂H₄ | OCH=CF₂ | F | H |
| CH₃CH=CHC₂H₄ | OCH=CF₂ | F | F |
| (CH₃)₂CH | OCH=CF₂ | H | H |
| (CH₃)₂CH | OCH=CF₂ | F | H |
| (CH₃)₂CH | OCH=CF₂ | F | F |
| (CH₃)₂CHCH₂ | OCH=CF₂ | H | H |
| (CH₃)₂CHCH₂ | OCH=CF₂ | F | H |
| (CH₃)₂CHCH₂ | OCH=CF₂ | F | F |
| CH₃ | CH=CF₂ | H | H |
| CH₃ | CH=CF₂ | F | H |
| CH₃ | CH=CF₂ | F | F |
| C₂H₅ | CH=CF₂ | H | H |
| C₂H₅ | CH=CF₂ | F | H |
| C₂H₅ | CH=CF₂ | F | F |
| n-C₃H₇ | CH=CF₂ | H | H |
| n-C₃H₇ | CH=CF₂ | F | H |
| n-C₃H₇ | CH=CF₂ | F | F |
| n-C₄H₉ | CH=CF₂ | H | H |
| n-C₄H₉ | CH=CF₂ | F | H |
| n-C₄H₉ | CH=CF₂ | F | F |
| n-C₅H₁₁ | CH=CF₂ | H | H |

-continued

| R¹ | R² | L¹ | L² |
|---|---|---|---|
| n-C₅H₁₁ | CH=CF₂ | F | H |
| n-C₅H₁₁ | CH=CF₂ | F | F |
| n-C₆H₁₃ | CH=CF₂ | H | H |
| n-C₆H₁₃ | CH=CF₂ | F | H |
| n-C₆H₁₃ | CH=CF₂ | F | F |
| CH₂=CH | CH=CF₂ | H | H |
| CH₂=CH | CH=CF₂ | F | H |
| CH₂=CH | CH=CF₂ | F | F |
| CH₃CH=CH | CH=CF₂ | H | H |
| CH₃CH=CH | CH=CF₂ | F | H |
| CH₃CH=CH | CH=CF₂ | F | F |
| CH₂=CHC₂H₄ | CH=CF₂ | H | H |
| CH₂=CHC₂H₄ | CH=CF₂ | F | H |
| CH₂=CHC₂H₄ | CH=CF₂ | F | F |
| CH₃CH=CHC₂H₄ | CH=CF₂ | H | H |
| CH₃CH=CHC₂H₄ | CH=CF₂ | F | H |
| CH₃CH=CHC₂H₄ | CH=CF₂ | F | F |
| (CH₃)₂CH | CH=CF₂ | H | H |
| (CH₃)₂CH | CH=CF₂ | F | H |
| (CH₃)₂CH | CH=CF₂ | F | F |
| (CH₃)₂CHCH₂ | CH=CF₂ | H | H |
| (CH₃)₂CHCH₂ | CH=CF₂ | F | H |
| (CH₃)₂CHCH₂ | CH=CF₂ | F | F |
| CH₃ | CF=CF₂ | H | H |
| CH₃ | CF=CF₂ | F | H |
| CH₃ | CF=CF₂ | F | F |
| C₂H₅ | CF=CF₂ | H | H |
| C₂H₅ | CF=CF₂ | F | H |
| C₂H₅ | CF=CF₂ | F | F |
| n-C₃H₇ | CF=CF₂ | H | H |
| n-C₃H₇ | CF=CF₂ | F | H |
| n-C₃H₇ | CF=CF₂ | F | F |
| n-C₄H₉ | CF=CF₂ | H | H |
| n-C₄H₉ | CF=CF₂ | F | H |
| n-C₄H₉ | CF=CF₂ | F | F |
| n-C₅H₁₁ | CF=CF₂ | H | H |
| n-C₅H₁₁ | CF=CF₂ | F | H |
| n-C₅H₁₁ | CF=CF₂ | F | F |
| n-C₆H₁₃ | CF=CF₂ | H | H |
| n-C₆H₁₃ | CF=CF₂ | F | H |
| n-C₆H₁₃ | CF=CF₂ | F | F |
| CH₂=CH | CF=CF₂ | H | H |
| CH₂=CH | CF=CF₂ | F | H |
| CH₂=CH | CF=CF₂ | F | F |
| CH₃CH=CH | CF=CF₂ | H | H |
| CH₃CH=CH | CF=CF₂ | F | H |
| CH₃CH=CH | CF=CF₂ | F | F |
| CH₂=CHC₂H₄ | CF=CF₂ | H | H |
| CH₂=CHC₂H₄ | CF=CF₂ | F | H |
| CH₂=CHC₂H₄ | CF=CF₂ | F | F |
| CH₃CH=CHC₂H₄ | CF=CF₂ | H | H |
| CH₃CH=CHC₂H₄ | CF=CF₂ | F | H |
| CH₃CH=CHC₂H₄ | CF=CF₂ | F | F |
| (CH₃)₂CH | CF=CF₂ | H | H |
| (CH₃)₂CH | CF=CF₂ | F | H |
| (CH₃)₂CH | CF=CF₂ | F | F |
| (CH₃)₂CHCH₂ | CF=CF₂ | H | H |
| (CH₃)₂CHCH₂ | CF=CF₂ | F | H |
| (CH₃)₂CHCH₂ | CF=CF₂ | F | F |
| CH₃ | OCF=CF₂ | H | H |
| CH₃ | OCF=CF₂ | F | H |
| CH₃ | OCF=CF₂ | F | F |
| C₂H₅ | OCF=CF₂ | H | H |
| C₂H₅ | OCF=CF₂ | F | H |
| C₂H₅ | OCF=CF₂ | F | F |
| n-C₃H₇ | OCF=CF₂ | H | H |
| n-C₃H₇ | OCF=CF₂ | F | H |
| n-C₃H₇ | OCF=CF₂ | F | F |
| n-C₄H₉ | OCF=CF₂ | H | H |
| n-C₄H₉ | OCF=CF₂ | F | H |
| n-C₄H₉ | OCF=CF₂ | F | F |
| n-C₅H₁₁ | OCF=CF₂ | H | H |
| n-C₅H₁₁ | OCF=CF₂ | F | H |
| n-C₅H₁₁ | OCF=CF₂ | F | F |
| n-C₆H₁₃ | OCF=CF₂ | H | H |
| n-C₆H₁₃ | OCF=CF₂ | F | H |
| n-C₆H₁₃ | OCF=CF₂ | F | F |
| CH₂=CH | OCF=CF₂ | H | H |
| CH₂=CH | OCF=CF₂ | F | H |
| CH₂=CH | OCF=CF₂ | F | F |
| CH₃CH=CH | OCF=CF₂ | H | H |
| CH₃CH=CH | OCF=CF₂ | F | H |
| CH₃CH=CH | OCF=CF₂ | F | F |
| CH₂=CHC₂H₄ | OCF=CF₂ | H | H |
| CH₂=CHC₂H₄ | OCF=CF₂ | F | H |
| CH₂=CHC₂H₄ | OCF=CF₂ | F | F |
| CH₃CH=CHC₂H₄ | OCF=CF₂ | H | H |
| CH₃CH=CHC₂H₄ | OCF=CF₂ | F | H |
| CH₃CH=CHC₂H₄ | OCF=CF₂ | F | F |
| (CH₃)₂CH | OCF=CF₂ | H | H |
| (CH₃)₂CH | OCF=CF₂ | F | H |
| (CH₃)₂CH | OCF=CF₂ | F | F |
| (CH₃)₂CHCH₂ | OCF=CF₂ | H | H |
| (CH₃)₂CHCH₂ | OCF=CF₂ | F | H |
| (CH₃)₂CHCH₂ | OCF=CF₂ | F | F |

EXAMPLES OF MIXTURES

Example M1

| | | | |
|---|---|---|---|
| BCH-3F.F | 10.80% | Clearing point [° C.]: | 98.2 |
| BCH-5F.F | 9.00% | d · Δn [μm]: | 0.50 |
| ECCP-30CF₃ | 4.50% | Δn [589 nm, 20° C.:] | 0.0954 |
| ECCP-50CF₃ | 4.50% | Δε [kHz, 20° C.]: | 5.7 |
| CBC-33F | 1.80% | γ1 [mPa · s, 20° C.]: | 150 |
| CBC-53F | 1.80% | d · Δn [μm]: | 0.50 |
| CBC-55F | 1.80% | Twist [°]: | 90 |
| PCH-6F | 7.20% | | |
| PCH-7F | 5.40% | | |
| CCP-20CF₃ | 7.20% | | |
| CCP-30CF₃ | 10.80% | | |
| CCP-40CF₃ | 6.30% | | |
| CCP-50CF₃ | 9.90% | | |
| PCH-5F | 9.00% | | |
| CWCZU-5-F | 10.00% | | |

Example M2

| | | | |
|---|---|---|---|
| CCP-2F.F.F | 11.00% | Clearing point [° C.]: | 86.4 |
| CCP-3F.F.F | 10.00% | Δn [589 nm, 20° C.:] | 0.0802 |
| CCP-30CF₃ | 6.00% | Δε [kHz, 20° C.]: | 10.6 |
| CGU-2-F | 11.00% | γ1 [mPa · s, 20° C.]: | 135 |
| CGU-3-F | 11.00% | d · Δn [μm]: | 0.50 |
| CGU-5-F | 9.00% | Twist [°]: | 90 |
| BCH-3F.F.F | 3.00% | | |
| CCZU-3-F | 15.00% | | |
| CWCZU-3-F | 11.00% | | |
| CWCZG-3-F | 10.00% | | |
| CWCZP-3-OT | 3.00% | | |

Example M3

| | | | |
|---|---|---|---|
| CCP-2F.F.F | 11.00% | Clearing point [° C.]: | 81.6 |
| CCP-3F.F.F | 10.00% | Δn [589 nm, 20° C.:] | 0.0818 |
| CCP-30CF₃ | 6.00% | Δε [kHz, 20° C.]: | 10.7 |
| CGU-2-F | 11.00% | γ1 [mPa · s, 20° C.]: | 133 |
| CGU-3-F | 11.00% | d · Δn [μm]: | 0.50 |
| CGU-5-F | 10.00% | Twist [°]: | 90 |
| BCH-3F.F.F | 5.00% | | |

-continued

| | |
|---|---|
| CCZU-3-F | 15.00% |
| CWCZU-3-F | 11.00% |
| CWCZG-3-OT | 10.00% |

Example M4

| | | | |
|---|---|---|---|
| PCH-7F | 2.00% | Clearing point [° C.]: | 82.5 |
| CCP-30CF$_3$ | 8.00% | Δn [589 nm, 20° C.:] | 0.0831 |
| CCP-20CF$_3$.F | 10.00% | Δε [kHz, 20° C.]: | 9.6 |
| CCP-30CF$_3$.F | 9.00% | γ1 [mPa · s, 20° C.]: | 161 |
| CCP-50CF$_3$.F | 12.00% | d · Δn [μm]: | 0.50 |
| CCP-2F.F.F | 12.00% | Twist [°]: | 90 |
| CCP-3F.F.F | 12.00% | | |
| CCP-5F.F.F | 6.00% | | |
| CGU-2-F | 5.00% | | |
| CGU-3-F | 6.00% | | |
| CGU-5-F | 9.00% | | |
| CBC-33F | 1.00% | | |
| CWCZU-3-F | 5.00% | | |
| CWCZG-3-OT | 3.00% | | |

Example M5

| | | | |
|---|---|---|---|
| CCP-2F.F.F | 12.00% | Clearing point [° C.]: | 96.6 |
| CCP-3F.F.F | 10.00% | Δn [589 nm, 20° C.:] | 0.0908 |
| CCP-30CF$_3$.F | 6.00% | Δε [kHz, 20° C.]: | 10.1 |
| CCP-20CF$_3$ | 6.00% | γ1 [mPa · s, 20° C.]: | 162 |
| CCP-30CF$_3$ | 9.00% | d · Δn [μm]: | 0.50 |
| CCP-50CF$_3$ | 4.00% | Twist [°]: | 90 |
| BCH-3F.F.F | 17.00% | | |
| BCH-5F.F.F | 10.00% | | |
| CCZU-3-F | 15.00% | | |
| CWCZU-3-F | 6.00% | | |
| CWCZG-3-OT | 5.00% | | |

Example M6

| | | | |
|---|---|---|---|
| CCP-2F.F.F | 12.00% | Clearing point [° C.]: | 91.1 |
| CCP-3F.F.F | 12.00% | Δn [589 nm, 20° C.:] | 0.0825 |
| CCP-30CF$_3$ | 3.00% | Δε [kHz, 20° C.]: | 10.2 |
| CCP-20CF$_3$ | 6.00% | γ1 [mPa · s, 20° C.]: | 151 |
| CCP-30CF$_3$ | 8.00% | d · Δn [μm]: | 0.50 |
| CCP-50CF$_3$ | 7.00% | Twist [°]: | 90 |
| CGU-2-F | 9.00% | | |
| CGU-3-F | 8.00% | | |
| CGU-5-F | 5.00% | | |
| CCZU-3-F | 15.00% | | |
| CWCZU-3-F | 6.00% | | |
| CWCZG-3-OT | 6.00% | | |
| CWCZP-3-OT | 2.00% | | |
| CC-3-V1 | 1.00% | | |

Example M7

| | | | |
|---|---|---|---|
| PCH-5F | 3.20% | Clearing point [° C.]: | 135.2 |
| CCP-20CF$_2$.F.F | 17.04% | | |
| CCP-30CF$_2$.F.F | 16.00% | | |
| CCP-50CF$_2$.F.F | 17.04% | | |
| CUP-2F.F | 5.36% | | |
| CUP-3F.F | 5.36% | | |

-continued

| | |
|---|---|
| CBC-33F | 5.36% |
| CBC-53F | 5.36% |
| CBC-55F | 5.28% |
| CWCZU-5-F | 20.02% |

Example M8

| | | | |
|---|---|---|---|
| CCH-301 | 11.21% | Clearing point [° C.]: | 96.8 |
| CCH-501 | 8.80% | | |
| CCP-2F.F.F | 8.00% | | |
| CCP-3F.F.F | 10.41% | | |
| CCP-5F.F.F | 4.00% | | |
| CCZU-2-F | 4.00% | | |
| CCZU-3-F | 13.61% | | |
| CCZU-5-F | 4.00% | | |
| CH-33 | 2.40% | | |
| CH-35 | 2.40% | | |
| CH-43 | 2.40% | | |
| CCPC-33 | 2.40% | | |
| CCH-3CF$_3$ | 6.40% | | |
| CWCZU-5-F | 19.96% | | |

Example M9

| | | | |
|---|---|---|---|
| CCH-301 | 7.40% | Clearing point [° C.]: | 121.8 |
| CCH-3CF$_3$ | 4.23% | Δn [589 nm, 20° C.:] | 0.0693 |
| CCH-501 | 5.82% | | |
| CCP-2F.F.F | 5.29% | | |
| CCP-3F.F.F | 6.87% | | |
| CCP-5F.F.F | 2.64% | | |
| CCPC-33 | 1.59% | | |
| CCZU-2-F | 2.64% | | |
| CCZU-3-F | 8.99% | | |
| CCZU-5-F | 2.64% | | |
| CH-33 | 1.59% | | |
| CH-35 | 1.59% | | |
| CH-43 | 1.59% | | |
| CWCZU-5-F | 47.12% | | |

Example M10

| | | | |
|---|---|---|---|
| BCH-3F.F | 10.80% | Δn [589 nm, 20° C.:] | +0.0954 |
| BCH-5F.F | 9.00% | Δε [kHz, 20° C.]: | +5.7 |
| ECCP-30CF$_3$ | 4.50% | | |
| ECCP-50CF$_3$ | 4.50% | | |
| CBC-33F | 1.80% | | |
| CBC-53F | 1.80% | | |
| CBC-55F | 1.80% | | |
| PCH-6F | 7.20% | | |
| PCH-7F | 5.40% | | |
| CCP-20CF$_3$ | 7.20% | | |
| CCP-30CF$_3$ | 10.80% | | |
| CCP-40CF$_3$ | 6.30% | | |
| CCP-50CF$_3$ | 9.90% | | |
| PCH-5F | 9.00% | | |
| CWCZU-5F | 10.00% | | |

Example M11

| | | | |
|---|---|---|---|
| CCH-301 | 11.21% | Clearing point [° C.]: | +96.8 |
| CCH-3CF$_3$ | 6.40% | Δε [kHz, 20° C.]: | +7.3 |
| CCH-501 | 8.80% | | |
| CCP-2F.F.F | 8.00% | | |
| CCP-3F.F.F | 10.41% | | |
| CCP-5F.F.F | 4.00% | | |
| CCPC-33 | 2.40% | | |
| CCZU-2-F | 4.00% | | |
| CCZU-3-F | 13.61% | | |
| CCZU-5-F | 4.00% | | |
| CH-33 | 2.40% | | |
| CH-35 | 2.40% | | |
| CH-43 | 2.40% | | |
| CWCZU-5-F | 19.96% | | |

Example M12

| | |
|---|---|
| CCP-2F.F.F | 11.00% |
| CCP-3F.F.F | 13.00% |
| CCP-5F.F.F | 6.00% |
| CCZU-2-F | 4.00% |
| CCZU-3-F | 16.00% |
| CCZU-5-F | 4.00% |
| CGU-2-F | 6.00% |
| CGU-3-F | 6.00% |
| CCH-3CF$_3$ | 4.00% |
| CCOC-4-3 | 2.00% |
| CWCZU-5-F | 28.00% |

Example M13

| | |
|---|---|
| CCH-301 | 23.00% |
| CCZU-2-F | 5.00% |
| CCZU-3-F | 19.00% |
| CCZU-5-F | 5.00% |
| CCPC-33 | 3.00% |
| CCPC-34 | 3.00% |
| CCPC-35 | 2.00% |
| CCOC-3-3 | 3.00% |
| CCOC-4-3 | 4.00% |
| CCOC-3-5 | 3.00% |
| CH-33 | 3.00% |
| CH-35 | 2.00% |
| CH-43 | 2.00% |
| CWCZU-5-F | 23.00% |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystalline compound of formula I,

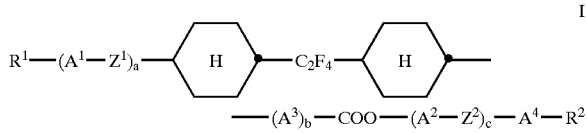

wherein $R^1$ is a straight-chain or branched alkyl radical having 1 to 15 C atoms which is unsubstituted, singly substituted by CN or CF$_3$, at least singly substituted by halogen, wherein optionally one or more CH$_2$ groups are substituted by —O—, —CO—, —S—, —CH=CH—, —C≡C—, —OC—O— or —O—CO— in such a way that O atoms are not directly linked together, $R^2$ is CN, SF$_5$, H, F, Cl, NCS, SCN or a straight-chain or branched alkyl radical having 1 to 15 C atoms which is unsubstituted, singly substituted by CN or CF$_3$, at least singly substituted by halogen, wherein optionally one or more CH$_2$ groups are substituted by —O—, —CO—, —S—, —CH=CH—, —C≡C—, —OC—O— or —O—CO— in such a way that O atoms are not directly linked together, $A^1$, $A^2$, $A^3$ and $A^4$ are each, independently, a 1,4-cyclohexenylene radical in which one or two non-adjacent CH$_2$ groups are optionally replaced by —O— or —S—, a 1,4-phenylene radical in which one or two CH groups are optionally replaced by N, or a radical selected from the group consisting of piperidine-1,4-diyl, 1,4-bicyclo[2.2.2]octylene, naphthalene-2,6-diyl, decahydronaphthalene-2,6-diyl, and 1,2,3,4-tetrahydronaphthalene-2,6-diyl, wherein each is optionally singly substituted or polysubstituted by halogen, $Z^1$ and $Z^2$ are each, independently, —CO—O—, —O—CO—, —CF$_2$O—, —OCF$_2$—, —CH$_2$O—, —OCH$_2$—, —CH$_2$CH$_2$—, —(CH$_2$)$_4$—, —C$_2$F$_4$—, —CF$_2$CH$_2$—, —CH$_2$CF$_2$—, —CF=CF—, —CH=CH—, —C≡C— or a single bond, a is 0, 1 or 2, b is 0, 1 or 2, and c is 0, 1 or 2, wherein a+b+c≦2.

2. A liquid-crystalline compound according to claim 1, wherein $R^1$ is a straight-chain alkyl radical of 1 to 10 C atoms or an alkenyl radical of 2 to 10 C atoms.

3. A liquid-crystalline compound according to claim 1, wherein $R^1$ and $R^2$ are, each independently, a straight-chain alkyl or alkoxy radical of 2 to 7 C atoms.

4. A liquid-crystalline compound according to claim 1, wherein $R^2$ is H, F, Cl, CN, CF$_3$, SF$_5$, CF$_2$H, OCF$_3$, OCF$_2$H, OCFHCF$_3$, OCFHCFH$_2$, OCFHCF$_2$H, OCF$_2$CH$_3$, OCF$_2$CFH$_2$, OCF$_2$CF$_2$H, OCF$_2$CF$_2$CF$_2$H, OCF$_2$CF$_2$CFH$_2$, OCFHCF$_2$CF$_3$, OCFHCF$_2$CF$_2$H, OCF$_2$CF$_2$CF$_3$, OCF$_2$CHFCF$_3$, or OCClFCF$_2$CF$_3$.

5. A liquid-crystalline compound according to claim 1, wherein $R^2$ is F, CN, OCF$_3$, OCHF$_2$, CF$_3$, OCHFCF$_3$, OC$_2$F$_5$, OCF$_2$CHFCF$_3$, or a straight-chain alkyl or alkoxy.

6. A liquid-crystalline compound according to claim 1, wherein c is 0.

7. A liquid-crystalline compound according to claim 1, wherein a is 0.

8. A liquid-crystalline compound according to claim 1, wherein $Z^1$ and $Z^2$ are, each independently, a single bond, —CF$_2$O—, —OCF$_2$—, —C$_2$F$_4$—, —CH$_2$O—, —OCH$_2$—, or —COO—.
9. A liquid-crystalline compound according to claim 1, which is of the formulae I1 to I24,
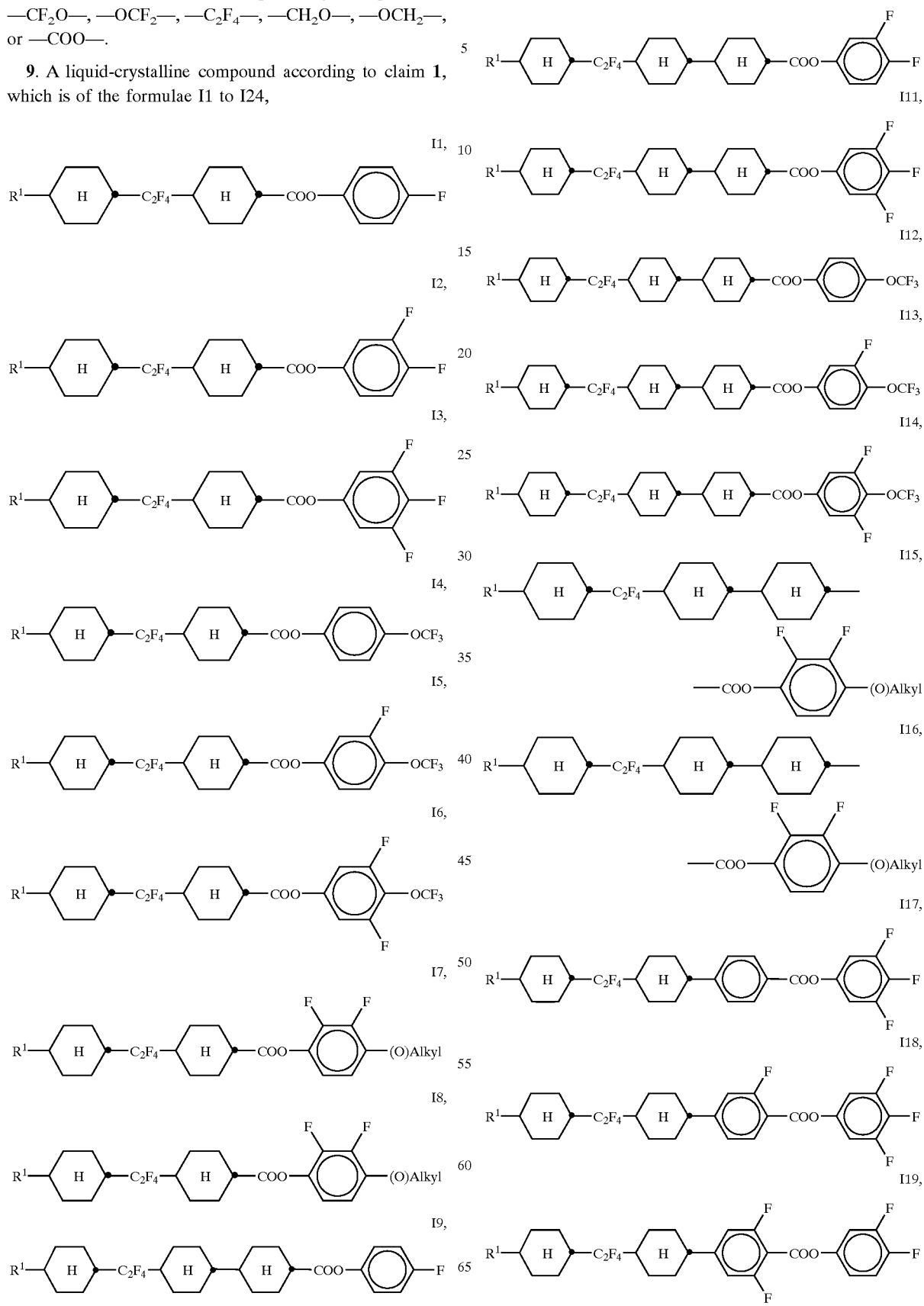

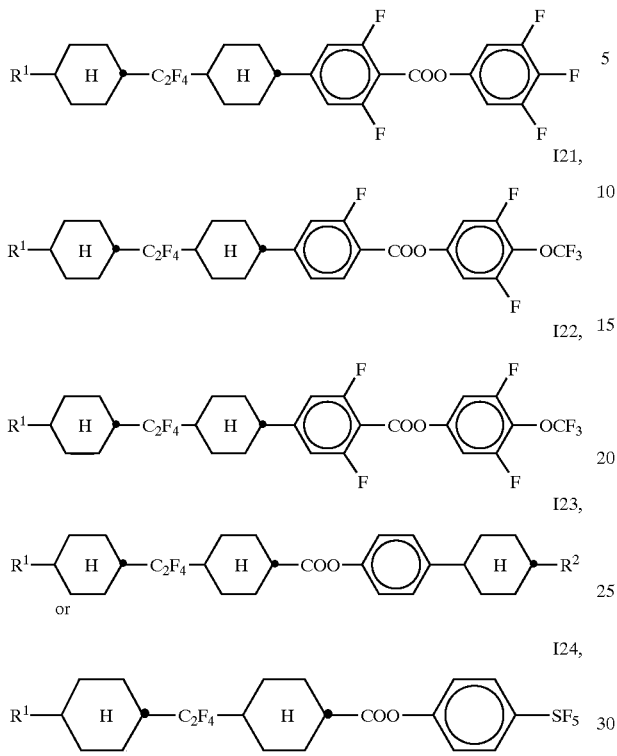

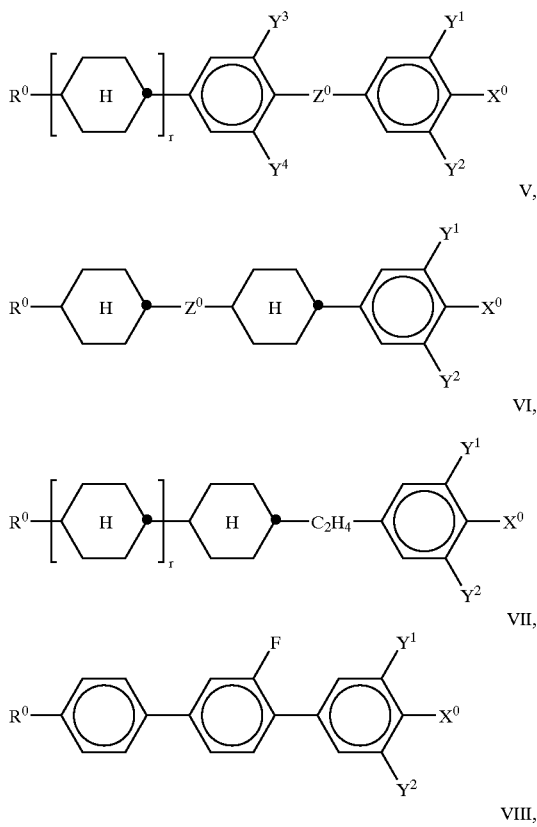

wherein

R[1] is a straight-chain or branched alkyl radical having 1 to 15 C atom which is unsubstituted, singly substituted by CN or CF$_3$, at least singly substituted by halogen, wherein optionally one or more CH$_2$ groups are substituted by —O—, —CO—, —S—, —CH=CH—, —C≡C—, —OC—O— or —O—CO— in such a way that O atoms are not directly linked together, and alkyl is a straight-chain or branched alkyl radical of 1–9 C atoms.

10. A liquid-crystalline medium, comprising at least one compound of formula I of claim 1 and at least one additional mesogenic compound.

11. A liquid-crystalline medium according to claim 10, further comprising one or more compounds of formulae II, III, IV, V, VI, VII, VIII, IX or X,

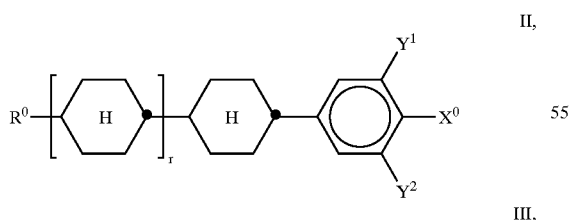

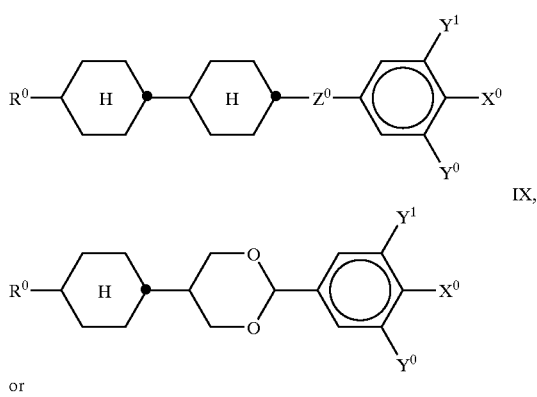

wherein

R[0] is n-alkyl, oxaalkyl, fluoroalkyl, alkenyloxy or alkenyl, each having up to 9 C atoms, X[0] is halogenated alkyl, halogenated alkenyl, halogenated alkenyloxy, halogenated alkoxy, each having up to 7 C atoms, F or Cl, $Z^0$ is —CH=CH—, —$C_2H_4$—, —$C_2F_4$—, —CF=CF—, —$CF_2O$—, —$OCF_2$— or —COO—, $Y^1$, $Y^2$, $Y^3$ and $Y^4$ are, each independently, H or F, and r is 0 or 1.

12. A liquid-crystalline medium according to claim 11, comprising at least 50 wt % of compounds of formulae I to X.

13. A liquid-crystalline medium according to claim 10, comprising 5 to 50 wt % at least one compound of formula I.

14. A liquid-crystaline medium according to claim 10, further comprising one or more compounds of formulae RI to RX,

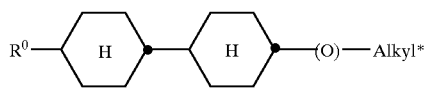
RI,

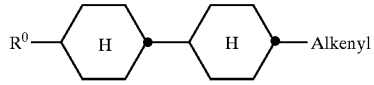
RII,

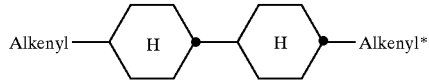
RIII,

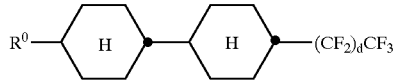
RIV,

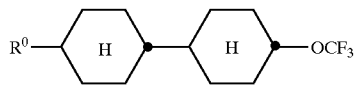
RV,

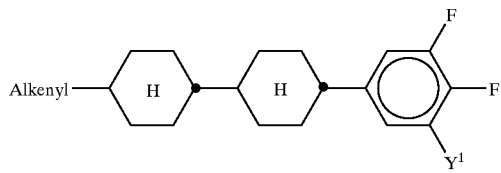
RVI,

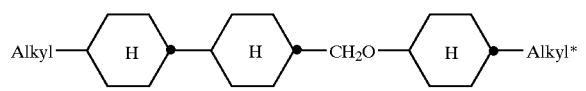
RVII,

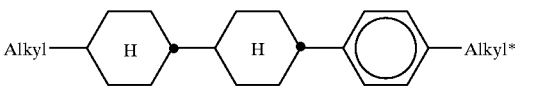
RVIII,

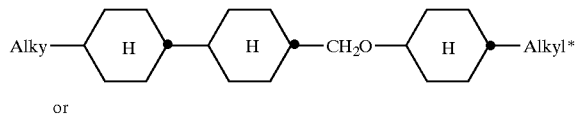
RIX, or

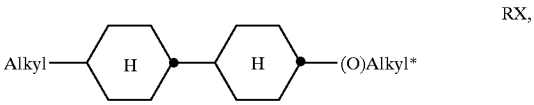
RX, wherein $R^0$ is n-alkyl, oxaalkyl, fluoroalkyl, alkenyloxy or alkenyl, each having up to 9 C atoms, d is 0, 1 or 2, $Y^1$ is H or F, Alkyl or Alkyl* is, each independently, a straight-chain or branched alkyl radical having 1–9 C atoms, and Alkenyl or Alkenyl* is, each independently, a straight-chain or branched alkenyl radical having up to 9 C atoms.

15. A liquid-crystalline medium according to claim 11, wherein $X^0$ is F, $OCHF_2$ or $OCF_3$.

16. In an electro-optical liquid-crystal display comprising a liquid-crystalline medium, the improvement wherein said medium contains a compound according to claim 1.

17. In a method of generating, an electro-optical effect using a liquid-crystal display, the improvement wherein said display is in accordance with claim 16.

* * * * *

UNITED STATES PATENT AND TRADEMARK OFFICE
CERTIFICATE OF CORRECTION

PATENT NO. : 6,706,338 B2  Page 1 of 1
APPLICATION NO. : 10/024501
DATED : March 16, 2004
INVENTOR(S) : Peer Kirsch It is certified that error appears in the above-identified patent and that said Letters Patent is hereby corrected as shown below:

Column 60, line 41, reads "$Y^0$" should read -- $Y^2$ --
Column 60, line 48, reads "$Y^0$" should read -- $Y^2$ --
Column 60, line 54 reads "

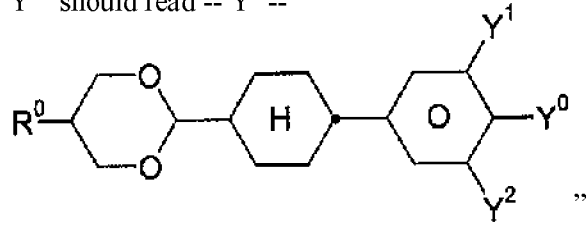

"

should read
--

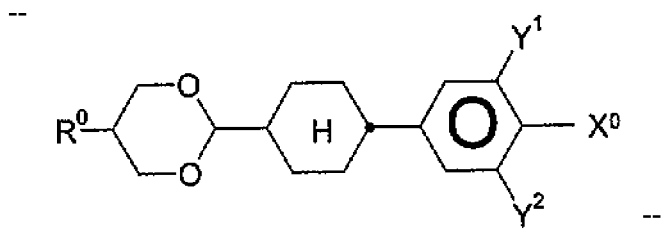

--

Column 62, line 10, reads "Alky" should read -- Alkyl --

Signed and Sealed this

Seventeenth Day of April, 2007

JON W. DUDAS
*Director of the United States Patent and Trademark Office*